US010555682B2

(12) United States Patent
Fokas et al.

(10) Patent No.: US 10,555,682 B2
(45) Date of Patent: Feb. 11, 2020

(54) SIGNAL PROCESSING METHODS

(71) Applicant: Cambridge Enterprise Limited, Cambridge (GB)

(72) Inventors: Athanassios Spyridon Fokas, Cambridge (GB); Parham Hashemzadeh, London (GB)

(73) Assignee: CAMBRIDGE ENTERPRISE LIMITED (GB)

( * ) Notice: Subject to any disclaimer, the term of this patent is extended or adjusted under 35 U.S.C. 154(b) by 484 days.

(21) Appl. No.: 15/315,746

(22) PCT Filed: Jun. 1, 2015

(86) PCT No.: PCT/GB2015/051597
§ 371 (c)(1),
(2) Date: Dec. 2, 2016

(87) PCT Pub. No.: WO2015/185911
PCT Pub. Date: Dec. 10, 2015

(65) Prior Publication Data
US 2017/0095174 A1    Apr. 6, 2017

(30) Foreign Application Priority Data
Jun. 2, 2014 (GB) .................................. 1409766.1

(51) Int. Cl.
*A61B 5/04* (2006.01)
*A61B 5/0476* (2006.01)
(Continued)

(52) U.S. Cl.
CPC ...... *A61B 5/04012* (2013.01); *A61B 5/04005* (2013.01); *A61B 5/0476* (2013.01);
(Continued)

(58) Field of Classification Search
CPC ... A61B 5/04; A61B 5/04001; A61B 5/04004; A61B 5/04005; A61B 5/04008;
(Continued)

(56) References Cited

U.S. PATENT DOCUMENTS 4,736,751 A * 4/1988 Gevins ................. A61B 5/0017
600/544
5,817,029 A * 10/1998 Gevins ................. A61B 5/0478
600/544
(Continued)

FOREIGN PATENT DOCUMENTS

EP    1 468 647 A1    10/2004
JP    2005-287675 A    10/2005

OTHER PUBLICATIONS

International Search Report and Written Opinion dated Aug. 28, 2015 in connection with International Application No. PCT/GB2015/051597.
(Continued)

*Primary Examiner* — Ahmed M Farah
(74) *Attorney, Agent, or Firm* — Tarolli, Sundheim, Covell & Tummino LLP

(57) ABSTRACT

We describe a method of processing an EEG and/or MEG signal to generate image data representing a 3D current distribution, J, within the brain, the method comprising: capturing a plurality of electric and/or magnetic measurements from the exterior of the head; solving an integral equation for a part of said current distribution to generate said image data representing said 3D current distribution, wherein said integral equation comprises an integral of a first function representing said part of said current distribution and of a second function ($\nabla_T v_s(r,\tau)$) representing the geometry and conductivity of the head independent of said current distribution; wherein said solving comprises: modelling the head as at least two regions separated by at least
(Continued)

one internal boundary, and solving a set of partial differential equations, one for each said internal region, each partial differential equation comprising a geometry-conductivity function (w(r,τ)) representing the geometry and conductivity of the respective region, wherein said solving is subject to a boundary condition that either i) the gradients of the functions across the or each said internal boundary are smooth when conductivity is taken into account, or ii) a normal component of the electric field of said part of said current distribution is continuous across the or each said internal boundary, and wherein said geometry-conductivity function for an outermost said region of said head defines said second function ($\nabla_T v_s(r,\tau)$).

19 Claims, 13 Drawing Sheets

(51) Int. Cl.
| | | |
|---|---|---|
| *G06T 7/11* | (2017.01) | |
| *G06T 7/73* | (2017.01) | |
| *G06T 7/13* | (2017.01) | |
| *A61B 5/00* | (2006.01) | |
| *G06T 7/00* | (2017.01) | |
| *G06T 7/60* | (2017.01) | |

(52) U.S. Cl.
CPC .......... *A61B 5/7239* (2013.01); *A61B 5/7242* (2013.01); *G06T 7/0012* (2013.01); *G06T 7/11* (2017.01); *G06T 7/13* (2017.01); *G06T 7/60* (2013.01); *G06T 7/73* (2017.01); *G06T 2207/30016* (2013.01)

(58) Field of Classification Search
CPC ... A61B 5/04012; A61B 5/0476; A61B 5/048; G06T 7/00; G06T 7/10; G06T 7/11; G06T 7/13; G06T 7/0012; G06T 7/60; G06T 7/62
USPC .......................................................... 600/544
See application file for complete search history.

(56) References Cited

U.S. PATENT DOCUMENTS

| | | | | |
|---|---|---|---|---|
| 7,956,974 | B2* | 6/2011 | Wakabayashi .... | G02F 1/134363 349/141 |
| 8,406,848 | B2* | 3/2013 | Wu ..................... | A61B 5/04007 600/407 |
| 8,724,864 | B2* | 5/2014 | Persson .................... | A61B 5/05 382/128 |
| 9,179,854 | B2* | 11/2015 | Doidge ................ | A61B 5/0476 |
| 2004/0116798 | A1* | 6/2004 | Cancro .............. | A61B 5/04009 600/409 |
| 2008/0097235 | A1* | 4/2008 | Ofek .................... | A61B 5/0484 600/544 |
| 2011/0313274 | A1* | 12/2011 | Subbarao ............ | A61B 5/04007 600/409 |
| 2013/0303934 | A1* | 11/2013 | Collura ................ | A61B 5/0482 600/545 |
| 2018/0055394 | A1* | 3/2018 | Sohrabpour ........ | A61B 5/04012 |
| 2018/0276822 | A1* | 9/2018 | Liu ....................... | A61B 5/0478 |

OTHER PUBLICATIONS

International Preliminary Report on Patentability dated Dec. 15, 2016 in connection with International Application No. PCT/GB2015/051597.
United Kingdom Search Report dated Mar. 10, 2015 in connection with Application No. GB 1409766.1.
Dassios et al., The definite non-uniqueness results for deterministic EEG and MEG data. Inverse Problems. May 2013;29(6):065012.
Fokas, Electro-magneto-encephalography for a three-shell model: distributed current in arbitrary, spherical and ellipsoidal geometries. Journal of the Royal Society Interface. May 6, 2009;6(34):479-88.
Fokas et al., Electro-magneto-encephalography for the three-shell model: numerical implementation via splines for distributed current in spherical geometry. Inverse Problems. Feb. 28, 2012;28(3):35009.
Huang et al., A novel integrated MEG and EEG analysis method for dipolar sources. NeuroImage. 2007;37:731-48.
Liang et al., Source reconstruction of brain electromagnetic fields—Source iteration of minimum norm (SIMN). NeuroImage. 2009;47:1301-11.

* cited by examiner

SIGNAL PROCESSING METHODS

RELATED APPLICATIONS

This application is a 371 U.S. National Stage Application of International Application No. PCT/GB2015/051597, entitled "SIGNAL PROCESSING METHODS," filed Jun. 1, 2015, which claims priority to Great Britain application no. 1409766.1, filed on Jun. 2, 2014, both of which are hereby incorporated by reference in their entirety for all purposes.

FIELD OF THE INVENTION

This invention relates to methods, apparatus, and computer program code for generating image data from EEG (electroencephalography) and/or MEG (magnetoencephalography) signals.

BACKGROUND TO THE INVENTION

Active neurons produce small currents whose basis is the change in the concentration of certain ions (ionic currents). The flow of current in the neural system produces a weak magnetic field. The measurement of this field outside the head and the estimation of the neuronal current which produced this field is called Magnetoencephalography (MEG). In spite of the fact that neuromagnetic signals are only of the order of 50-500 fT, it is still possible to measure them using the superconductivity quantum interference device. Electroencephalography (EEG) measures the electric potential on the scalp. Although EEG plays a significant role in clinical practice especially in epilepsy, it is not routinely used to produce images depicting the areas of the brain which are more active; such images are produced via MEG. In order to produce images of brain activation using either MEG or EEG it is necessary to solve certain mathematical inverse problems. The relevant inverse problems for MEG and EEG involve the calculation of the neuronal current from the knowledge of the magnetic field and of the electric potential, respectively. Currently there exist two main approaches for the solution of the above inverse problems: 1. Dipole Models. Here it is assumed that the neuronal current is localized only at a small number of points. At each of these points the current is expressed in terms of a dipole characterized by the location $T_j$ and the moment $Q_j$, j=1; 2; . . . N, where N is small, and the constants $\{Q_j, \tau_j\}_1^N$ are to be determined. The magnetic field and the electric potential are computed starting with the above current, and then the constants $\{Q_j, \tau_j\}_1^N$ are adjusted step by step minimizing a certain natural cost function. 2. Distributed Models. Here the continuous current is approximated again via a sum of dipoles, but now N is very large of the order of 1000 to 10,000. Then, the procedure is similar to the one described for dipole models.

The first, dipole models approach described above is based on the assumption that a small number of dipoles is sufficient for modelling the neuronal current. The unknown parameters are the positions and orientations of these dipoles and these are adjusted to minimize the mismatch between the values of the electric potential in the case of EEG, and of the magnetic field in the case of MEG generated by the dipoles and the actual measurements. However these methods rely on local optimisation and suffer from getting trapped by local minima. Furthermore, they require the assumption that the number of dipoles is less than the number of sensors. The second, distributed source modelling approach divides the cerebrum into voxels each representing a possible of location of a current source (there is no a priori assumption regarding the number of dipoles), and the objective is to find a configuration of activity at these locations which is consistent with the measurements. However there exists an infinite number of distributions of current sources which can generate the same scalp electric potential and the same magnetic field outside the head and thus the inverse problem is highly ill-posed. This in turn necessitates the use of various assumptions which are often inappropriate; the technique also suffers from 'cross-talk' in that the activity at an arbitrary location is contaminated by activity from other brain regions.

One of the inventors finally provided a solution to the non-uniqueness problem, which is fundamental to reconstructing a current distribution based on MEG/EEG: although it is not possible to uniquely reconstruct the current in a conductor from knowledge of the electric potential on its boundary, or of magnetic field outside the conductor it is possible to determine which part of the current can be reconstructed via MEG and/or EEG. This solution is described in "Electro-magneto-encephalography for a Three-shell Model: Distributed Current in Arbitrary, Spherical and Ellipsoidal Geometries", A S Fokas, *J. R. Soc. Interface*, 6:479-488, 2009. Further background prior art can be found in A S Fokas et al., "Electro-magneto-encephalography for the Three-shell Model: numerical implementation via splines for distributed current in spherical geometries", *Inverse Problems*, 28, 2012. General background can be found in Liang et al., "Source reconstruction of brain electromagnetic fields", Neuroimage, 27:1301-1311, 2009; Huang et al., "A novel integrated MEG and EEG analysis method for dipolar sources", Neuroimage, 37:731-748, 2007; EP1468647; and JP2005/287675A.

The primary neuronal current distribution $J^P$ (T) is specified by three components of the current. This can be modelled by a combination of a scalar function, $\psi$, and a vector function A (altogether) with the constraint that the divergence of A is zero (giving 3 independent components). The use of EEG provides information about $\psi$, more particular the electric potential on the scalp can be represented by a combination of $\psi$ and a second function $v_s$ (where s denotes the surface of the scalp). The use of MEG provides information about A; more particularly the MEG signal can be modelled by a combination of $\psi$ and A, in combination with an auxiliary (vector) function H. Both H and $v_s$ are independent of the current distribution and depend only on the geometry and conductivity of the head.

The function H, is derivable from $v_s$. In addition Fokas identified a set of partial differential equations whose solution defines $v_s$ (equations 2.11-2.14 in the paper, ibid). These are adumbrated below (renumbered as 0.11 et seq):

$$\nabla^2 u_c(r, \tau) = 0, r \in \Omega_c, \tau \in \Omega_c, \tag{0.11}$$

$$\frac{\partial}{\partial n}\left[\frac{1}{|r-\tau|} + v_c(r, \tau)\right] = \sigma_f \frac{\partial v_f(r, \tau)}{\partial n}, r \in \partial \Omega_c;$$

$$\nabla^2 v_f(r, \tau) = 0, r \in \Omega_f, \tau \in \Omega_c, \tag{0.12}$$

$$v_f(r, \tau) = \frac{1}{\sigma_c}\left[\frac{1}{|r-\tau|} + v_c(r, \tau)\right], r \in \partial \Omega_c,$$

$$\sigma_f \frac{\partial v_f(r, \tau)}{\partial n} = \sigma_b \frac{\partial v_b(r, \tau)}{\partial n}, r \in \partial \Omega_f, \tau \in \Omega_c;$$

$$\nabla^2 v_b(r, \tau) = 0, r \in \Omega_b, \tau \in \Omega_c, \tag{0.13}$$

$$v_b(r, \tau) = v_f(r, \tau), r \in \partial \Omega_f,$$

$$\sigma_b \frac{\partial v_b(r, \tau)}{\partial n} = \sigma_s \frac{\partial v_s(r, \tau)}{\partial n}, r \in \partial \Omega_b, \tau \in \Omega_c;$$

$$\nabla^2 v_s(r, \tau) = 0, r \in \Omega_s, \tau \in \Omega_c, \tag{0.14}$$

$$v_s(r, \tau) = v_b(r, \tau), r \in \partial \Omega_b,$$

$$\frac{\partial v_s(r, \tau)}{\partial n} = 0, r \in \partial \Omega_s.$$

In the above equations $\Omega$ denotes a three-dimensional space occupied by a conducting medium and $\partial\Omega$ its boundary. The head is modelled as four regions, a central region $\Omega_c$ occupied by the cerebrum/brain (subscript c), around which are located three shells, $\Omega_f$, $\Omega_b$, and $\Omega_s$, respectively, modelling the spaces occupied by the cerebrospinal fluid (subscript f), the skull (subscript b), and the skin/scalp (subscript s). The region external to the head is denoted $\Omega_e$. In the equations $\partial\Omega_c$, $\partial\Omega_f$, $\partial\Omega_b$, and $\partial\Omega_s$ denote the smooth boundaries of the domains $\Omega_c$, $\Omega_f$, $\Omega_b$, and $\Omega_s$, respectively. Each region has a respective electrical conductivity $Y_c$, $\sigma_f$, $\sigma_b$, $\sigma_s$; the magnetic permeability is $\mu$. The r vector ($r \in R^3$) denotes position; later the (primary) neuronal current, the magnetic field, and the electric potential are denoted $J^P(r)$, $B(r)$ and $u(r)$ respectively. Similarly $\tau$ denotes a position vector within $\Omega_c$ (where the primary current, $J^P(r)$, is defined). The derivative $$\frac{\partial}{\partial n}$$

denotes differentiation along the direction of $\hat{n}$ where the hat denotes a unit vector and $\hat{n}$ denotes the unit vector outward normal to the surface $\partial\Omega$. As stated above, equations (0.11)-(0.14) are independent of the current $J^P(\tau)$ and depend only on the geometry and on the conductivities $\sigma_c$, $\sigma_b$, $\sigma_f$ and $\sigma_s$.

The skilled person will appreciate that to solve a set of partial differential equations the information needed comprises the equations, the respective domains of the equations, and the boundary conditions, as given above. Solving the above equations would lead to a value for $v_s$, which could then be used to solve the inverse problem for EEG and/or MEG. However there is a problem in that the above equations cannot readily be solved.

SUMMARY OF THE INVENTION

According to an aspect of the present invention there is therefore provided a method of processing an EEG and/or MEG signal to generate image data representing a 3D current distribution, J, within the brain, the method comprising: capturing a plurality of electric and/or magnetic measurements from the exterior of the head; solving an integral equation for a part of said current distribution to generate said image data representing said 3D current distribution, wherein said integral equation comprises an integral of a first function representing said part of said current distribution and of a second function ($\nabla_\tau v_s(r,\tau)$) representing the geometry and conductivity of the head independent of said current distribution; wherein said solving comprises: modelling the head as at least two regions separated by at least one internal boundary, and solving a set of partial differential equations, one for each said internal region, each partial differential equation comprising a geometry-conductivity function ($w(r,\tau)$) representing the geometry and conductivity of the respective region, wherein said solving is subject to a boundary condition that either i) the gradients of the functions across the or each said internal boundary are smooth when conductivity is taken into account, or ii) a normal component of the electric field of said part of said current distribution, is continuous across the or each said internal boundary, and wherein said geometry-conductivity function for an outermost said region of said head defines said second function ($\nabla_\tau v_s(r,\tau)$).

Broadly speaking, the inventors have recognised that the previously described equations can be solved if they are recast into a different form, in particular one which avoids the problematical boundary condition of equation 0.11 above (in embodiments, the set of partial differential equations 15-18 given later). Thus in embodiments of the invention the equations are modified so that each is subject to a boundary condition that there is continuity of the normal component of the electric field across a region boundary, in other words that the gradients of the functions across the/or each internal boundary are smooth when conductivity is taken into account. This in turn changes the initial partial differential equation for the innermost region (equation 0.11 above) from a Laplace's equation to a Poisson's equation form, that is the right hand side of the equation is a function rather than zero. This, however, is a tractable form. Moreover when expressed in this way the set of partial differential equations effectively expresses the functions v defined in terms of the fields generated from a monopole source rather than fields generated by a dipole source (as is the case for equations 0.11-0.14).

The geometry-conductivity function w is proportional to the gradient of the function v in equations 0.11-0.14, which is consistent with the observation that the potential of a dipole is the directional derivative of the potential of a monopole. More particularly, in embodiments the geometry-conductivity function for the outermost region of the head ($w_s$) is proportional to the second function referred to above (the second function being the gradient of the previously described function v).

In embodiments the set of partial differential equations comprises a partial differential equation for an innermost said region in the Poisson equation form $\sigma_c \nabla^2 w_c \propto \nabla \cdot Q\delta(r-\tau)$, where r is a position vector within said innermost region, $\tau$ is a dummy variable, Q is a charge, $\delta$ is the delta function, $w_c$ is the geometry-conductivity function for the innermost region and $\sigma_c$ is an electrical conductivity of the innermost region. The partial differential equations for subsequent successively more outer regions j then have the Laplace equation form $\nabla^2 w_j = 0$. In embodiments the boundary conditions define that $$\sigma_{j-1} \frac{\partial w_{j-1}}{\partial n} = \sigma_j \frac{\partial w_j}{\partial n}$$

where j−1 denotes a region within region j, and where n denotes a unit vector outward normal to the surface of the boundary between regions j−1 and j.

The integral equation(s) solved to determine a part of the current distribution depends upon whether EEG data and/or MEG data is being processed. In either case, however, once the relevant part or parts of the current distribution have been determined data representing this distribution may be used directly as the image data, representing the data in any convenient manner—for example overlaying the data on a 3D representation of a head/brain and/or on a 2D slice through a head/brain.

The integral equation solved for an EEG signal is:

$$u_s(r) = -\frac{1}{4\pi} \int_{\Omega_c} (\nabla^2 \Psi(\tau)) v_s(r, \tau) dV(\tau), \quad r \in \partial\Omega_s,$$

where $u_s(r)$ defines measured electric potential on a boundary of the outermost region of the head (the scalp) at position r, $\Omega_c$ defines the innermost, cerebrum region, $\Omega_s$ defines a surface of the outermost, scalp region, $v_s(r,\tau)$ is an integral of said second geometry-conductivity function $\nabla_\tau v_s(r,\tau)$ for the outermost, scalp region. Here $\omega$ is a scalar value representing an irrotational part of the 3D current distribution ($\psi$ is determined by solving the inverse problem).

The integral equation solved for an MEG signal is:

$$\frac{4\pi}{\mu} B(r) \cdot r = -\int_{\Omega_c} \nabla^2(\tau \cdot A(\tau)) \frac{dV(\tau)}{|r-\tau|} + \frac{1}{4\pi} \int_{\Omega_c} (\nabla^2 \Psi(\tau)) r \cdot H(r,\tau) dV(\tau) \quad r \in \Omega_e,$$

where $B(r)$ defines a measured magnetic field at a sensor position r, $\Omega_c$ defines the innermost, cerebrum region of the head, and $\Omega_e$ defines the external region beyond the head. Here $H(r,\tau)$ is a vectorial geometry-conductivity function for the head, defined by the geometry-conductivity functions for the modelled regions of said head (w $(r,\tau)$). This integral also uses the scalar value $\psi$ (which may be determined from an EEG signal), and in addition depends on $\tau \cdot A(\tau)$, which defines a radial component of a solenoidal part of the 3D current distribution (here $\tau \cdot A(\tau)$ is determined by solving the inverse problem).

The skilled person will recognise that, in solving an integral equation of the above type, the equation need not be solved in the form written above and may be re-arranged or rewritten, and equivalently solved in a different form. For example the EEG integral equation given above may be rewritten using Green's theorem as follows:

$$u_s(r) = \frac{1}{4\pi} \int_{\Omega_c} \nabla \Psi(\tau) \cdot \nabla_\tau v_s(r,\tau) dV(\tau), \quad r \in \partial \Omega_s$$

Similarly the MEG integral equation above may be rewritten using Green's theorem as:

$$\frac{4\pi}{\mu} B(r) \cdot r = -\int_{\Omega_c} \nabla^2(\tau \cdot A(\tau)) \frac{dV(\tau)}{|r-\tau|} - \frac{1}{4\pi} \sum_{l \in \{1,2,3\}} \int_{\Omega_c} r_l [\nabla \Psi(\tau) \cdot \nabla_\tau H_l(r,\tau)] dV(\tau), \quad r \in \Omega_e.$$

To facilitate solving the inverse problem for MEG the inventors have recognised that the above integral equation may usefully be rewritten as follows:

$$\int_{\Omega_c} \nabla^2(\tau \cdot A(\tau)) \frac{dV(\tau)}{|r-\tau|} = -\frac{1}{4\pi} \sum_{l \in \{1,2,3\}} \int_{\Omega_c} r_l [\nabla \Psi(\tau) \cdot \nabla_\tau H_l(r,\tau)] dV(\tau) - \frac{4\pi}{\mu} B(r) \cdot r$$

In some preferred implementations of the technique the inverse problem is solved for EEG by determining the scalar value $\psi$ representing an irrotational part of the 3D current distribution by writing $\psi$ in terms of a set of basis functions having respective unknown coefficients $\lambda_i$ defined by a vector $\lambda$. In some preferred embodiments radial basis functions are employed, which is convenient, but the skilled person will appreciate that other basis functions may also be employed. Such an expansion enables the integral equation to be reformulated as a set of equations represented by a matrix equation:

$$b = E \cdot \lambda$$

where b comprises a vector of the electric potential measurements on the scalp. This is straightforward to solve to determine an estimate of $\lambda$ using a least squares approach. In the above matrix equation the matrix E has the substantial advantage that elements of the matrix depend only on the geometry and conductivity of the model of the head (and the basic functions). Thus although relatively computationally expensive to calculate, the elements of matrix E may be pre-computed and stored for use in solving the EEG inverse problem. Broadly speaking, determining an estimate for $\lambda$ then reduces to a matrix inversion. The skilled person will appreciate that there are many different techniques which may be employed to solve the above matrix equation.

It will be appreciated that, depending upon the accuracy of the desired results, the model of the head may be more or less complicated—that is although it incorporates a model of the cerebrum (brain) one or more of the subsequent shells may be omitted, albeit it is preferable to represent each of the cerebrospinal fluid (CSF), the bone of the skull, and the skin of the scalp. Interestingly, and counter-intuitively, the elements of matrix E may be pre-computed for one or more generic head models, thus avoiding the need to determine the particular geometry of the head of a patient under examination, for example by MRI (magnetic resonance imaging) scan or the like. Nonetheless it is preferable to have an exact model of the head geometry for accuracy; the conductivity values used for the different regions of the head are essentially standard.

When modelling an MEG signal it is preferable to also capture EEG data and then use this to estimate the scalar component of the current distribution, $\psi$ (from $\lambda$). In addition a second, related set of geometryconductivity functions H can be calculated from the set of geometry-conductivity functions v (or w). A similar matrix equation to that given above can then be written for the MEG data (for example from SQUID measurements), as follows.

A radial component of the solenoidal part of the 3D current distribution, $\tau \cdot A(\tau)$, is expanded in terms of basis functions, again radial basis functions in preferred embodiments, these functions having coefficients defined by a vector $\beta$. Then $$M\beta = c$$

where c comprises a vector representation of the magnetic field measurements, $B(r_i)$, at sensor positions $r_i$. For increased accuracy the vector c preferably also includes a term dependent on the scalar function iv, in particular in combination with the previously described (current distribution-independent) vectorial geometry-conductivity function $H(r,\tau)$ (determined from the geometry-conductivity functions for the modelled head regions, $w(r,\tau)$).

Like E, M need only be computed once for a particular head and then stored for subsequent use; or a generic M may be used for all heads or heads of a particular type, for example size and/or shape). As before, the skilled person will be aware of many techniques which may be employed to solve the matrix equation to estimate a value for $\beta$, including for example a least squares method, and hence to derive an estimate of the solenoidal part of the current distribution.

The invention further provides processor control code to implement the above-described methods, for example on a general purpose computer system or on a digital signal processor (DSP). The code is provided on a non-transitory physical data carrier such as a disk, CD- or DVD-ROM, programmed memory such as non-volatile memory (eg Flash) or read-only memory (Firmware). Code (and/or data) to implement embodiments of the invention may comprise source, object or executable code in a conventional programming language (interpreted or compiled) such as C, or assembly code, or code for a hardware description language. As the skilled person will appreciate such code and/or data may be distributed between a pluralities of coupled components in communication with one another.

In a related aspect the invention provides a system for processing an EEG and/or MEG signal to generate image data representing a 3D current distribution, J, within the brain, the system comprising: an input to receive a plurality of captured electric and/or magnetic measurements from the exterior of the head; and a processor coupled to said input, to an output, to working memory and to program memory storing processor control code, wherein the stored code comprises code to: solve an integral equation for a part of said current distribution to generate said image data representing said 3D current distribution, wherein said integral equation comprises an integral of a first function representing said part of said current distribution and of a second function ($\nabla_\tau v_s(r,\tau)$) representing the geometry and conductivity of the head independent of said current distribution; wherein said solving comprises: modelling the head as at least two regions separated by at least one internal boundary, and solving a set of partial differential equations, one for each said internal region, each partial differential equation comprising a geometry-conductivity function ($w(r,\tau)$) representing the geometry and conductivity of the respective region, wherein said solving is subject to a boundary condition that either i) the gradients of the functions across the or each said internal boundary are smooth when conductivity is taken into account, or ii) a normal component of the electric field of said part of said current distribution is continuous across the or each said internal boundary, and wherein said geometry-conductivity function for an outermost said region of said head defines said second function ($\nabla_\tau v_s(r,\tau)$); and output said image data, wherein said image data comprises data representing a part of said 3D current distribution.

In embodiments the system is implemented on a general purpose computer system coupled to an EEG and/or MEG system to obtain the input data for processing. Alternatively the system may be built into an EEG and/or MEG system. Still further alternatively the system may be remote from an EEG and/or MEG system, for example on a computer network or in the 'cloud' to provide EEG and/or MEG signal processing as a service. Still further alternatively the system may be implemented in electronic circuitry or other hardware, for example using a digital signal processor and/or one or more ASICs (application specific integrated circuits).

As previously described the output image data may simply comprise data representing the determined irrotational and/or solenoidal part of the current distribution J. The data may be output to a screen, printer, over the network, or in any other suitable manner. The data may be visualised, for example as an overlay on a 3D image of the head or brain and/or on a 2D section of a head/brain.

In a further related aspect the invention provides a method of processing an EEG signal to generate image data representing a 3D current distribution, J, within the brain, the method comprising: capturing a plurality of measurements of electric potential on the scalp (b); and using a representation of a part of said current distribution as an expansion having a series of unknown coefficients, $\lambda$, of expansion basis functions, where b is dependent on a product of a matrix E and $\lambda$, and where E represents the geometry and conductivity of the head independent of said current distribution, wherein said geometry includes at least one internal boundary within the head, solving an equation combining b and E·$\lambda$ to determine an estimate of $\lambda$, wherein $\lambda$ defines said 3D current distribution; wherein E·$\lambda$ represents $$\int_{\Omega_c}(\nabla^2\Psi(\tau))v_s(r,\tau)dV(\tau)$$

where $\psi$ is a scalar value representing J, where $v_s(r,\tau)$ is a function representing the geometry and conductivity of the head independent of said current distribution, $\Omega_c$ denotes the region of the brain over which the current distribution is determined, r lies on the surface of the scalp on which EEG measurements are made, and r is a dummy variable; and wherein, in said matrix E, a value of an element of the matrix E is defined by an integral, over a region including said current distribution, of a gradient of a said expansion basis function and a function $w_s(r,\tau)$ representing $v_s(r,\tau)$; where $w_s(r,\tau)$ alternatively represents the geometry and conductivity of the head independent of said current distribution, wherein a function $w(r,\tau)$ is determined for each internal region of the head defined by said at least one internal boundary, wherein $w_s(r,\tau)$ is the outermost said function $w(r,\tau)$, and wherein $w_s(r,\tau)$ is determined subject to the constraint that, when conductivity is taken into account, the gradients of the functions $w(r,\tau)$ on either side of different regions of the head separated by a said internal boundary are smooth across each said internal boundary such that a normal component of electric field is continuous across each said internal boundary; and generating image data representing said 3D current distribution from said estimate of $\lambda$.

Again, in embodiments the above described boundary conditions apply across each internal boundary of the head; using a set of partial differential equations with this set of boundary conditions makes the problem tractable.

In a complementary aspect the invention provides a system for processing an EEG signal to generate image data representing a 3D current distribution, J, within the brain, the system comprising: an input to receive a plurality of measurements of electric potential on the scalp (b); and a processor coupled to said input, to an output, to working memory and to program memory storing processor control code, wherein the stored code comprises code to: use a representation of a part of said current distribution as an expansion having a series of unknown coefficients, $\lambda$, of expansion basis functions, where b is dependent on a product of a matrix E and $\lambda$, and where E represents the geometry and conductivity of the head independent of said current distribution, wherein said geometry includes at least one internal boundary within the head, to solve an equation combining b and E·$\lambda$ to determine an estimate of $\lambda$, wherein $\lambda$ defines said 3D current distribution; wherein E·$\lambda$ represents $$\int_{\Omega_c}(\nabla^2\Psi(\tau))v_s(r,\tau)dV(\tau)$$

where $\psi$ is a scalar value representing J, where $v_s(r,\tau)$ is a function representing the geometry and conductivity of the head independent of said current distribution, $\Omega_c$ denotes the region of the brain over which the current distribution is determined, r lies on the surface of the scalp on which EEG measurements are made, and T is a dummy variable; and wherein, in said matrix E, a value of an element of the matrix E is defined by an integral, over a region including said current distribution, of a gradient of a said expansion basis function and a function $w_s(r,\tau)$ representing $v_s(r,\tau)$; where $w_s(r,\tau)$ alternatively represents the geometry and conductivity of the head independent of said current distribution, wherein a function $w(r,\tau)$ is determined for each internal region of the head defined by said at least one internal boundary, wherein $w_s(r,\tau)$ is the outermost said function $w(r,\tau)$, and wherein $w_s(r,\tau)$ is determined subject to the constraint that, when conductivity is taken into account, the gradients of the functions $w(r,\tau)$ on either side of different regions of the head separated by a said internal boundary are smooth across each said internal boundary such that a normal component of electric field is continuous across each said internal boundary; and output image data representing said 3D current distribution determined from said estimate of $\lambda$.

In a further related aspect the invention provides A method of processing an EEG and/or MEG signal to generate data representing an image of a 3D current distribution, J, within the brain, the method comprising: capturing a plurality of electric and/or magnetic measurements b from the exterior of the head; and determining a representation of a part of said 3D current distribution by determining an estimate of $\lambda$ in $b = E \cdot \lambda$, where $\lambda$ comprises a vector of coefficients of basis functions in an expansion of a scalar value, $\psi$, representing said part of said 3D current distribution, wherein b comprises a vector representing said measurements, and E is a matrix with elements $E(i, j)$ which represent the geometry and conductivity of a head independent of said 3D current distribution; and outputting data defining a representation of said part of said 3D current distribution, to provide data representing an image of said 3D current distribution.

Again the matrix elements may be computed as previously described. Thus embodiments of the method may include precomputing and storing matrix E prior to capturing the measurements. Optionally the same precomputed and stored matrix E may be used for a plurality of different determinations of 3D current distributions for a plurality of different heads or versions of matrix E may be for a set of generic head types and/or sizes and/or shapes.

In embodiments a value of an element $E(i, j)$ of the matrix E is defined by an integral, over a region including the current distribution, of a gradient of a jth basis function and a function $w_s(r,\tau)$, where $w_s(r,\tau)$ represents the geometry and conductivity of an outermost said region of said head at position $r_i$, independent of said current distribution. Preferably radial basis functions are employed.

The functions $w(r,\tau)$ for each internal region of the head are preferably determined by solving a set of partial differential equations for a set of functions $w_j(r,\tau)$, one for each region j. In preferred embodiments the partial differential equation each said region except the innermost comprises Laplace's equation for the respective function $w_j(r,\tau)$, and the partial differential equation for the innermost said region comprises Poisson's equation for the innermost region function $w_{innermost}(r,\tau)$. In preferred embodiments the solving is subject to a boundary condition that across each internal boundary a normal component of the electric field is continuous.

In preferred embodiments $E \cdot \lambda$ represents $$\int_{\Omega_c} (\nabla^2 \Psi(\tau)) v_s(r,\tau) dV(\tau)$$

where $\psi$ is a scalar value representing an irrotational part of J, where $v_s(r,\tau)$ is a function, dependent on $w_s(r,\tau)$, representing the geometry and conductivity of the head independent of the current distribution, $\Omega_c$ denotes the region of the brain over which the current distribution is determined, r lies on the surface of the scalp on which EEG measurements are made, and T is a dummy variable. Then the data representing an image of said 3D current distribution may comprise or consist of data representing of $\psi$. Preferably then b comprises a vector representation of said measurements of electric potential, $b(r_i)$ at positions $r_i$.

The invention also provides a non-transitory medium such as a disk or memory storing processor control code to implement the method. Again code (and/or data) to implement embodiments of the invention may comprise source, object or executable code in a conventional programming language (interpreted or compiled) such as C, or assembly code, or code for a hardware description language. As the skilled person will appreciate such code and/or data may be distributed between a plurality of coupled components in communication with one another.

In a complementary aspect the invention provides a system for processing an EEG and/or MEG signal to generate data representing an image of a 3D current distribution, J, within the brain, the system comprising: an input to receive a plurality of electric and/or magnetic measurements b from the exterior of the head; and a processor coupled to said input, to an output, to working memory and to program memory storing processor control code, wherein the stored code comprises code to: determine a representation of a part of said 3D current distribution by determining an estimate of $\lambda$ in $b = E \cdot \lambda$, where $\lambda$ comprises a vector of coefficients of basis functions in an expansion of a scalar value, $\psi$, representing said part of said 3D current distribution, wherein b comprises a vector representing said measurements, and E is a matrix with elements $E(i, j)$ which represent the geometry and conductivity of a head independent of said 3D current distribution; and output data defining a representation of said part of said 3D current distribution, to provide data representing an image of said 3D current distribution.

BRIEF DESCRIPTION OF THE DRAWINGS

These and other aspects of the invention will now be further described, by way of example only, with reference to the accompanying figures in which.

DETAILED DESCRIPTION OF PREFERRED EMBODIMENTS

1. Framework

Figures 1A, 1B:
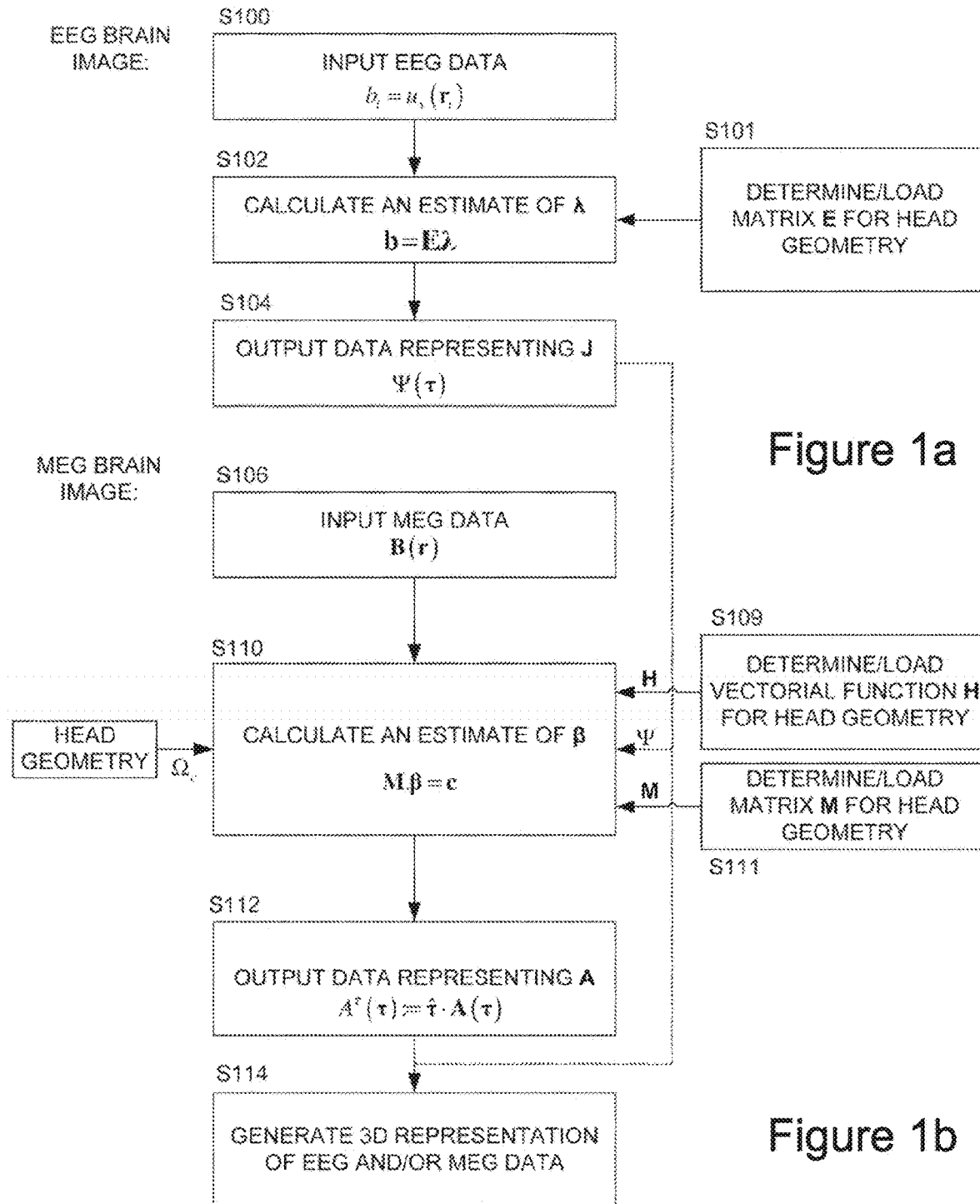
FIGS. 1a to 1d show, respectively, a flow diagram of a computer procedure for solving an inverse EEG problem according to an embodiment of the invention, a flow diagram of a computer procedure for solving an inverse MEG problem according to an embodiment of the invention, a flow diagram of a computer procedure for solving a set of partial differential equations to determine a matrix E and/or vectorial function H for use in numerically solving an inverse EEG/MEG problem according to embodiments of the invention, and a computer system programmed to implement the methods of FIGS. 1a to 1c.

In the following description we denote a domain and its conductivity by $\Omega \subset R^3$ and $\sigma$ respectively. Let the bounded domain $\Omega_c$ represent the cerebrum, which has conductivity $\sigma_c$. A shell $\Omega_f$ with conductivity $\sigma_f$, representing the cerebrospinal fluid (CSF), surrounds the domain $\Omega_c$. The CSF is surrounded by the skull characterized by the domain $\Omega_b$ with conductivity $\sigma_b$. Finally, the skull is surrounded by the scalp, which is modelled as a shell $\Omega_s$ with conductivity $\sigma_s$. The domain exterior to the head is denoted by $\Omega_e$ which is not conductive. The permeability of all domains is equal to the permeability $\mu_0$ of empty space. Let $J^p(\tau)$, $\tau \in \Omega_c$, denote the current which is supported within the cerebrum $\Omega_c$. For the above situation of arbitrary geometry and arbitrary current, it is shown in A S Fokas (*J. R. Soc. Interface*, 6:479-488, 2009, ibid) that the irrotational part of the current, which is denoted by the scalar function $\Psi(\tau)$, contributes to both the electric potential on the scalp and to the magnetic field in $\Omega_e$. On the other hand, the solenoidal part of the current, which is denoted by the vectorial function $A(\tau)$, does not affect the electric potential and furthermore only the radial component of $A(\tau)$ affects the magnetic field in $\Omega_e$.

Being more precise, an arbitrary vectorial function with support $\Omega_c$, can be expressed as $$J^p(\tau) = \nabla \Psi(\tau) + \nabla \times A(\tau), \quad \tau \in \Omega_c, \tag{1}$$

where $A(\tau)$ satisfies the constraint $\nabla \cdot A(\tau) = 0$. This constraint implies that $J^p(\tau)$ involves three arbitrary scalar functions, namely the scalar function $\Psi(\tau)$ and the two independent scalar functions characterizing $A(\tau)$.

It is shown in A S Fokas (*J. R. Soc. Interface*, 6:479-488, 2009, ibid) that the electric potential on the scalp is given by the expression $$u_s(r) = -\frac{1}{4\pi} \int_{\Omega_c} (\nabla^2 \Psi(\tau)) v_s(r, \tau) dV(\tau), \quad r \in \partial \Omega_s, \tag{2}$$

where $\partial \Omega_s$ denotes the surface of the scalp, i.e the smooth boundary of the domain $\Omega_s$. Here, $v_s(r,\tau)$ denotes a harmonic function which is independent of the current; it depends only on the geometry and on the conductivities. It is clear from equation (2) that the electric potential $u_s(r)$ depends only on the Laplacian of the irrotational part $(\Psi(\tau))$ of the current. It was also shown in A S Fokas (*J. R. Soc. Interface*, 6:479-488, 2009, ibid) that the measured magnetic field in $\Omega_e$ is given by the expression $$\frac{4\pi}{\mu} B(r) \cdot r = \tag{3}$$

$$-\int_{\Omega_c} \nabla^2 (\tau \cdot A(\tau)) \frac{dV(\tau)}{|r - \tau|} + \frac{1}{4\pi} \int_{\Omega_c} (\nabla^2 \Psi(\tau)) r \cdot H(r, \tau) dV(\tau) \quad r \in \Omega_e,$$

where $H(r,\tau)$ depends only on the geometry and on the conductivities; it is independent of the current. It is clear from equation (3) that in MEG the radial component of the magnetic field is affected by $\Psi(\tau)$ as well as by the radial component $\tau \cdot A(\tau)$ of the solenoidal part of the current.

We can use Green's first identity to rewrite equations (2) and (3) in the form $$u_s(r) = \frac{1}{4\pi} \int_{\Omega_c} \nabla \Psi(\tau) \cdot \nabla_\tau v_s(r, \tau) dV(\tau), \quad r \in \partial \Omega_s \tag{4}$$

and $$\frac{4\pi}{\mu} B(r) \cdot r = -\int_{\Omega_c} \nabla^2 (\tau \cdot A(\tau)) \frac{dV(\tau)}{|r - \tau|} - \tag{5}$$

$$\frac{1}{4\pi} \sum_{l \in \{1,2,3\}} \int_{\Omega_c} r_l [\nabla \Psi(\tau) \cdot \nabla_\tau H_l(r, \tau)] dV(\tau), \quad r \in \Omega_e.$$

Equations (4) and (5) follow from equations (2) and (3) by employing the following identities $\int_{\Omega_c} [H_l(r,\tau) \nabla_\tau^2 \Psi(\tau) + \nabla_\tau H_l(r,\tau) \cdot \nabla_\tau \Psi(\tau)] dV(\tau) = \oint_{\partial \Omega_c} [\nabla_\tau \Psi(\tau) \cdot \hat{n}] H_l(r,\tau) dS(\tau) i \in \{1,2,3\}$, $\oint_{\partial \Omega_c} H_l(r,\tau) [\nabla_\tau \Psi(\tau) \cdot \hat{n}] dS(\tau) = 0, i \in \{1,2,3\}$, $\oint_{\partial \Omega_c} v_s(r,\tau) [\nabla_\tau \Psi(\tau) \cdot \hat{n}_s] dS(\tau) = 0, \tag{6}$ where $\{H_1, H_2, H_3\}$ denote the Cartesian coordinates of $H(r,\tau)$.

We here present a general framework for obtaining the maximum possible information for the current, or more precisely for the part of the current that affects EEG and MEG, namely $$\nabla \Psi(\tau) \text{ and } \nabla^2 [\tau \cdot A(\tau)], \tau \in \Omega_c, \tag{7}$$

from the knowledge of the quantities measured in EEG and in MEG, namely the functions $$u_s(r) r \in \partial \Omega_s, \text{ and } r \cdot B(r) \ r \in \Omega_e, \tag{8}$$

respectively. This framework is based on (a) equations (4) and (5), and (b) on the existence of fast and accurate codes for the numerical computation of the auxiliary functions $v_s(r,\tau)$ and $H(r,\tau)$. Furthermore, we implement this general approach to a realistic three shell geometry.

2. Construction of $v_s(r,\tau)$, and $H(r,\tau)$

In order to analyse the basic equations (4) and (5) we first construct the functions $$v_s(r,\tau) r \in \partial \Omega_s, \tau \in \Omega_c, \text{ and } H(r,\tau) r \in \Omega_e, \tau \in \Omega_c. \tag{9}$$

The function $v_s(r,\tau)$ is a harmonic function which is obtained via the solution of the following system of equations:

$$\nabla^2 v_c(r, \tau) = 0, r \in \Omega_c, \tau \in \Omega_c, \tag{10}$$

$$\frac{\partial}{\partial n} \left[ \frac{1}{|r - \tau|} + v_c(r, \tau) \right] = \sigma_f \frac{\partial v_f(r, \tau)}{\partial n}, r \in \partial \Omega_c;$$

$$\nabla^2 v_f(r, \tau) = 0, r \in \Omega_f, \tau \in \Omega_c, \tag{11}$$

$$v_f(r, \tau) = \frac{1}{\sigma_c} \left[ \frac{1}{|r - \tau|} + v_c(r, \tau) \right], r \in \partial \Omega_c,$$

$$\sigma_f \frac{\partial v_f(r, \tau)}{\partial n} = \sigma_b \frac{\partial v_b(r, \tau)}{\partial n}, r \in \partial \Omega_f, \tau \in \Omega_c;$$

$$\nabla^2 v_b(r, \tau) = 0, r \in \Omega_b, \tau \in \Omega_c, \tag{12}$$

$$v_b(r, \tau) = v_f(r, \tau), r \in \partial \Omega_f,$$

$$\sigma_b \frac{\partial v_b(r, \tau)}{\partial n} = \sigma_s \frac{\partial v_s(r, \tau)}{\partial n}, r \in \partial \Omega_b, \tau \in \Omega_c;$$

$$\nabla^2 v_s(r,\tau) = 0, r \in \Omega_s, \tau \in \Omega_c, \qquad (13)$$
$$v_s(r,\tau) = v_b(r,\tau), r \in \partial\Omega_b,$$
$$\frac{\partial v_s(r,\tau)}{\partial n} = 0, r \in \partial\Omega_s.$$

In the above equations, $\partial\Omega_c$, $\partial\Omega_b$, $\partial\Omega_f$ and $\partial\Omega_s$ denote the smooth boundaries of the domains $\Omega_c$, $\Omega_b$, $\Omega_f$ and $\Omega_s$, respectively.

As stated earlier, equations (10)-(13) are independent of the current $J^P(\tau)$ and depend only on the geometry and on the conductivities $\sigma_c$, $\sigma_b$, $\sigma_f$ and $\sigma_s$. However, it turns out that it is convenient to construct the functions $v(r,\tau)$ via first constructing certain functions $u_j(r,\tau)$ which are defined in terms of a monopole source. Here the functions $u_j(r,\tau)$ represent the geometry-conductivity functions denoted $w(r,\tau)$ in the summary of the invention section and the claims (here $j \in \{c, f, b, s\}$ denoting the cerebrum, cerebrospinal fluid, bone and scalp respectively). The function $u_s(r,\tau)$ should not be confused with the EEG measurements as a function of position, $u_s(r_j)$.

The boundary condition of equation (10) makes the set of partial differential equations extremely difficult to solve. However in the functions below this boundary condition has been simplified by changing, and although this means that the partial differential equation for the cerebrum no longer has a Laplacian form, overall the problem becomes tractable: Let the functions $$u_j(r,\tau), r \in \Omega_j, \tau \in \Omega_c, j \in \{c,f,b,s\}, \qquad (14)$$

satisfy the following equations:

$$\sigma_c \nabla^2 u_c(r) = \nabla \cdot Q\delta(r - \tau), r \in \Omega_c, \qquad (15)$$
$$\sigma_c \frac{\partial u_c}{\partial n} = \sigma_f \frac{\partial u_f(r)}{\partial n}, r \in \partial\Omega_c;$$

$$\nabla^2 u_f(r) = 0, r \in \Omega_f, \qquad (16)$$
$$u_f(r) = u_c(r), r \in \partial\Omega_c,$$
$$\sigma_f \frac{\partial u_f(r)}{\partial n} = \sigma_b \frac{\partial u_b}{\partial n}, r \in \partial\Omega_f;$$

$$\nabla^2 u_b(r) = 0, r \in \Omega_b, \qquad (17)$$
$$u_b(r) = u_f(r), r \in \partial\Omega_f,$$
$$\sigma_b \frac{\partial u_b(r)}{\partial n} = \sigma_s \frac{\partial u_b(r)}{\partial n}, r \in \partial\Omega_b;$$

$$\nabla^2 u_s(r) = 0, r \in \Omega_s, \qquad (18)$$
$$u_s(r) = u_b(r), r \in \partial\Omega_b,$$
$$\frac{\partial u_s(r)}{\partial n} = 0, r \in \partial\Omega_s.$$

Then $u_j$ and $v_j$ are related by the equation $$u_j(r,\tau) = \frac{1}{4\pi} Q(\tau) \cdot \nabla_\tau v_j(r,\tau), \qquad (19)$$
$$j \in \{f, b, s\}, r \in \Omega_j, \tau \in \Omega_c.$$

Equation (19) above is consistent with the fact that the potential of a dipole is the directional derivative of the potential of a monopole.

2.1 Spherical Geometry

The advantage of constructing the function $v_s(r,\tau)$ via $u_s(r,\tau)$ becomes clear by considering the particular case of spherical geometry. In this case, a closed form expression for $v_s(r,\tau)$ can be derived, which involves the inversion of a 7×7 matrix. It was observed in Fokas et al., *Inverse Problems*, 28, 2012 (ibid) that this matrix is ill conditioned and requires regularization. On the hand, for the case of N spherical layers, with N arbitrary, a closed form expression for $u_s(r,\tau)$ can be obtained. This approach is straightforward and does not require matrix inversion. Indeed, let $r_1 < r_2 < \ldots < r_{N-1} < r_N$, and let $\sigma_1, \ldots, \sigma_N$ denote the radii and the corresponding conductivities of the domains $\Omega_1, \ldots, \Omega_N$. We consider a single dipole source characterized by $(Q,\tau)$. The position vector of the observation point is denoted by r. Let us introduce the following notations:

$$\hat{\tau} = \frac{\tau}{|\tau|}, \hat{r} = \frac{r}{|r|}, \qquad (20)$$
$$\cos(\alpha) = \hat{\tau} \cdot \hat{Q}, \cos(\gamma) = \hat{\tau} \cdot \hat{r}, \cos(\beta) = (\hat{\tau} \times \hat{Q}) \cdot (\hat{\tau} \times \hat{r}).$$

The observed potential at r is given by the following expression:

$$u_s(r,\tau) = \frac{|Q|}{4\pi\sigma_N r^2} \qquad (21)$$
$$\sum_{n=1}^{\infty} \left(\frac{\tau}{r}\right)^{n-1} \left[\frac{2n+1}{nM_{2,2} + (1+n)M_{2,1}}\right] \times [n\cos(\alpha)P_n[\cos(\gamma)] + \cos(\beta)\sin(\alpha)P_n^1[\cos(\gamma)]],$$

where the 2×2 matrix M is given by $$\begin{bmatrix} M_{1,1} & M_{1,2} \\ M_{2,1} & M_{2,2} \end{bmatrix} = \begin{bmatrix} 1 \\ (2n+1)^{N-1} \end{bmatrix} \qquad (22)$$
$$\prod_{k=1}^{N-1} \begin{bmatrix} n + (n+1)\frac{\sigma_k}{\sigma_{k+1}} & (n+1)\left(\frac{\sigma_k}{\sigma_{k+1}} - 1\right)\left(\frac{r}{r_k}\right)^{2n+1} \\ n\left(\frac{\sigma_k}{\sigma_{k+1}} - 1\right)\left(\frac{r_k}{r}\right)^{2n+1} & n + 1 + \frac{n\sigma_k}{\sigma_{k+1}} \end{bmatrix}.$$

Noting that $v_s(r,\tau)$ can be expressed in the form below (A S Fokas, *J. R. Soc. Interface*, 6:479-488, 2009, ibid)

$$v_s(r,\tau) = \sum_{n=1}^{\infty} H_n \frac{2n+1}{4\pi} \frac{\tau^n}{r^{n+1}} P_n(\hat{\tau} \cdot \hat{r}), \qquad (23)$$

where the unknown coefficients $H_n$ can be computed by inverting the 7×7 matrix mentioned earlier. By using equations (19) and (23) we bypass this inversion and can directly obtain $v_s(r,\tau)$ in closed form:

$$v_s(r,\tau) = \sum_{n=1}^{\infty} \left[\frac{2n+1}{nM_{2,2} + (1+n)M_{2,1}}\right] \frac{1}{\sigma_N} \frac{\tau^n}{r^{n+1}} P_n(\hat{\tau} \cdot \hat{r}). \qquad (24)$$

2.2 Arbitrary Geometry

In the case of arbitrary geometry, there exists (open source) code suitable for the numerical solution of equations (15)-(18), for example Zeynep Akalm-Acar and Scott Makeig, "Neuroelectromagnetic forward head modeling toolbox", *J Neurosci Methods*, 190(2):258-270, 2010. The numerical construction of $v_s(r,\tau)$ involves the following steps:

1. Fix a source point $\tau:=[\tau_1, \tau_2, \tau_3] \in \Omega_c$ and an observation point $r \in \partial\Omega_s$. Consider three dipoles positioned at the source $\tau \in \Omega_c$, with the following orthogonal moments:

2. $Q_1=[1,0,0], Q_2=[0,1,0], Q_3=[0,0,1].$ (25)

3. For each of the above three dipoles, solve the boundary value problem described by equations (15)-(18). We denote the solution for the potential due to the dipole oriented in the direction $Q_i$ by $u_s(r,\tau;Q_i)$. We define the vector 4. $u_s(r,\tau):[u_s(r,\tau;Q_1)u_s(r,\tau;Q_2)u_s(r,\tau;Q_3)]$ (26)

5. We obtain the gradient of $v_s(r,\tau)$ from equation $\nabla_\tau v_s(r,\tau) = 4\pi u_s(r,\tau).$ (27)

6. Then, by using the gradient theorem, we can compute $v_s(r,\tau)$ from the equation $v_s(r,\tau) - v_s(r,0) = \int_{[0,\tau]} \nabla_\tau v_s(r,l) \cdot dl.$ (28)

7. We can approximate the solution of the above equation by the expression $$v_s(r,\tau) \approx 4\pi \sum_{i=1}^{N} l_i u(r, \tau_i) \cdot \hat{\tau},$$ (29)

8. where $\tau = (l_1 + \ldots + l_N)\hat{\tau}$.
9. We repeat the above steps $\forall \tau \equiv \Omega_c, r \in \partial\Omega_s$. It should be noted that for a given dipole characterized by $(Q,\tau)$, most existing numerical solvers provide the solution for all discrete points $r \in \partial\Omega_s$ in a single run.

2.3 Construction of $H(r,\tau)$

The vectorial function $H(r,\tau)$ is uniquely defined in terms of the scalar functions $v_j(r,\tau)$:

$$H(r;\tau) = \int_{\partial\Omega_c} \left[\frac{1}{|r'-\tau|} + v_c(r',\tau) - \sigma_f v_f(r',\tau)\right]\left[\hat{n}(r') \times \nabla_{r'} \frac{1}{|r-r'|}\right]dS(r') + \int_{\partial\Omega_f}(\sigma_f v_f(r',\tau) - \sigma_b v_b(r',\tau))\left[\hat{n}(r') \times \nabla_{r'} \frac{1}{|r-r'|}\right]dS(r') + \int_{\partial\Omega_b}(\sigma_b v_b(r',\tau) - \sigma_s v_s(r',\tau))\left[\hat{n}(r') \times \nabla_{r'} \frac{1}{|r-r'|}\right]dS(r') + \sigma_s \int_{\partial\Omega_s} v_s(r',\tau)\left[\hat{n}(r') \times \nabla_{r'} \frac{1}{|r-r'|}\right]dS(r') \quad r \in \Omega_e, \tau \in \Omega_c.$$ (30)

2.3.1 Construction of $\nabla_\tau H(r,\tau)$ in Spherical Geometry

In the particular case of the multi-layer spherical geometry, an analytical expression for the magnetic field due to a dipole characterized by $(Q,\tau)$ is as follows:

$$B(r,\tau;Q) = \frac{\mu_0}{4\pi F^2(r,\tau)}(F(r,\tau)Q \times \tau - (Q \times \tau) \cdot [r\nabla_r F(r,\tau)]),$$ (31)

where $F(r,\tau)$ and $\nabla_r F(r,\tau)$ are given by $$F(r,\tau) = d(rd + r^2 - (\tau \cdot r)),$$ (32)

$$\nabla_r F(r,\tau) = \left(\frac{d^2}{r} + \frac{(r-\tau)\cdot r}{d} + 2d + 2r\right)r - \left(d + 2r + \frac{(r-\tau)\cdot r}{d}\right)\tau,$$

$$d := |r-\tau|, r = |r|.$$

For arbitrary geometry, an expression for the magnetic field due to a dipole characterized by $(Q(\tau),\tau)$ was derived in A S Fokas *J. R. Soc. Interface*, 6:479-488, 2009, ibid:

$$\frac{4\pi}{\mu}B(r,\tau;Q) = Q(\tau) \times \nabla_r \frac{1}{|r-\tau|} - \frac{1}{4\pi}Q(\tau) \cdot \nabla_\tau H(r,\tau),$$ (33)

where $H(r,\tau)$ is the vectorial function defined in equation (30). The gradient $\nabla_\tau H(r,\tau)$ is the following 3×3 matrix:

$$\nabla_\tau H(r,\tau) = \begin{pmatrix} \frac{\partial H_1}{\partial \tau_1} & \frac{\partial H_2}{\partial \tau_1} & \frac{\partial H_3}{\partial \tau_1} \\ \frac{\partial H_1}{\partial \tau_2} & \frac{\partial H_2}{\partial \tau_2} & \frac{\partial H_3}{\partial \tau_2} \\ \frac{\partial H_1}{\partial \tau_3} & \frac{\partial H_2}{\partial \tau_3} & \frac{\partial H_3}{\partial \tau_3} \end{pmatrix}.$$ (34)

Using equations (31) and (33), it is straightforward to show that $$\frac{\partial H_j}{\partial \tau_i} = 4\pi\left[Q_i \times \nabla_\tau \frac{1}{|r-\tau|}\right] \cdot Q_j - \frac{(4\pi)^2}{\mu}B(r,\tau;Q_i) \cdot Q_j,$$ (35)

$i, j \in \{1, 2, 3\}.$

2.3.2 Numerical Construction of $H(r,\tau)$

There exists several numerical solvers for computing the magnetic field problem due to a dipole or a collection of dipoles, for example Zeynep Akalm-Scott et al., ibid. In what follows, we outline a strategy to compute $H(\tau,r)$ using an existing solver. We denote by $B(r,\tau;Q)$ the solution of the magnetic field due to a dipole characterized by $(\tau,Q)$.

1. Fix a source point $\tau := [\tau_1, \tau_2, \tau_3] \in \Omega_c$ and an observation point $r \in \Omega_e$. Consider three dipoles positioned at the source $\tau \in \Omega_c$ with the following orthogonal moments:

2. $Q_1=[1,0,0], Q_2=[0,1,0], Q_3=[0,0,1].$ (36)

3. For each of the above three dipoles, solve the magnetic field problem. We denote by $B(r,\tau;Q_i)$ the solution of the magnetic field associated with the dipole oriented in the direction $Q_i$.

4. We can now compute the elements of the matrix $\nabla_\tau H(\tau,r)$ using the expression (16).

5. Repeat the above steps for $\forall \tau \Sigma \Omega_c$, and for all sensors positions $r_i \in \Omega_e$, where i denotes the ith sensor. The existing numerical solvers (ibid) compute the magnetic field at all sensors positions in a single run.

6. The gradient theorem, $H_j(\tau,r) - H_j(0,r) = \int_{[0,\tau]} \nabla_\tau H_j(l,r) \cdot dl \ j \in \{1,2,3\},$ (37)

7. can be employed to compute the components of the vectorial function $H(r,\tau)$.

2.4 Radial Basis Functions

Consider the Beppo-Levi space of distributions with square integrable second derivatives. This space is equipped with a rotation invariant semi norm: If $s \in BL^{(2)}(R^3)$ then this norm is defined by $$\|s\|^2 = \int_{R^3} \left[ \left(\frac{\partial^2 s(x)}{\partial x^2}\right)^2 + \left(\frac{\partial^2 s(x)}{\partial y^2}\right)^2 + \left(\frac{\partial^2 s(x)}{\partial z^2}\right)^2 \right] dxdydz + \int_{R^3} \left[ 2\left(\frac{\partial^2 s(x)}{\partial x \partial y}\right)^2 + 2\left(\frac{\partial^2 s(x)}{\partial x \partial z}\right)^2 + 2\left(\frac{\partial^2 s(x)}{\partial y \partial z}\right)^2 \right] dxdydz. \quad (38)$$

Consider the following interpolation problem: Given a set of distinct nodes $X=\{x_i\}_{i=1}^N$, and function values $\{f_i\}_{i=1}^N$, we construct an interpolation function $s(x)$ such that $$s(x_i)=f_i, \, i=1, \ldots, N. \quad (39)$$

By employing radial basis functions (RBF), an interpolation function can be expressed in the form $$s(x) = p(x) + \sum_{i=1}^N \lambda_i \varphi(\|x - x_i\|), \quad (40)$$

where $p(x)$ is the polynomial $$p(x)=c_1+c_2 x+c_3 y+c_4 z. \quad (41)$$

In this setting, $\{\lambda_i:1\leq i\leq N\}$ and $\{c_1, \ldots, c_4\}$, are coefficients to be determined, whereas $\varphi(r): R \to [0,\infty)$. Particular choices for the functions $\varphi(r)$ include $\varphi(r)=r$, $\varphi(r)=e^{-ar^2}$, $\varphi(r)=(r^2+c^2)^{1/2}$, and $\varphi(r)=r^2 \log(r)$. The smoothest interpolant is given by $$s^*(x) = p(x) + \sum_{i=1}^N \lambda_i \|x - x_i\|. \quad (42)$$

In certain problems, the following constraint is also imposed $$\sum_{i=1}^N \lambda_i p(x_i) = 0. \quad (43)$$

For EEG, $f=\psi(\tau)$, and for MEG, $f=\tau A^\tau(\tau)$. The unknown coefficients $\lambda_1, \ldots \lambda_N, c_1, \ldots, c_4$, are linearly related to the function $f(x)$, thus the interpolation problem reduces to the following least squares problem:

$$\begin{bmatrix} A & P \\ P^T & 0 \end{bmatrix} \begin{bmatrix} \lambda \\ c \end{bmatrix} = \begin{bmatrix} f \\ 0 \end{bmatrix}, \quad (44)$$

where the matrix $A \in R^{N \times N}$, is defined by $$A_{i,j}=\varphi(\|x_i-x_j\|) \quad (45)$$

and every row of the matrix $P \in R^{N \times 4}$ is defined as $$P(i,.)=[1 \, x_i \, y_i \, z_i] \, 1 \leq i \leq N. \quad (46)$$

3. The Inverse Problem for EEG

We analyse equation (4). A radial basis function approximation of $\Psi(\tau)$ can be written in the form $$\Psi(\tau) = \sum_{j=1}^N \lambda_j \varphi(\|\tau - \tau_j\|), \quad (47)$$

where $\varphi(\|\tau-\tau_j\|)=(\|\tau-\tau_j\|^2+c^2)^{1/2}$. Here, $\{\lambda_j:1\leq i\leq N\}$ are the coefficients to be estimated, and $c>0$ is a constant.

By substituting equation (47) into equation (4) we can formulate the following least squares problem:

$$b=E\lambda, \quad (48)$$

where $$E(i,j)=\int_{\Omega_c}[\nabla_\tau \varphi(\|\tau-\tau_j\|) \cdot u_s(r_i, \tau)]dV(\tau),$$

$$b(i)=u_s(r_i) \quad (49)$$

and i denotes the ith sensor index. We can compute the volume integral of equation (49) numerically. The parametrization of the problem acts as an implicit regularization. We assume that the measurements are corrupted by additive noise. In this setting, the maximum likelihood estimate (MLE) yields $$\hat{\lambda}=(E^T C_w^{-1} E)^{-1} E^T C_w^{-1} b, \quad (50)$$

where $C_w$ is the covariance matrix of the measurement noise or the sample covariance matrix. The volume integrals of equation (49) are computationally expensive. However, this computation can be parallelized. More precisely, for every matrix entry (i, j), the process of solving the volume integral is independent from every other matrix entry. Furthermore, for a given geometry, the matrix E in equation (49) needs to be computed only once.

Optionally, since head geometries are similar, an approximate result may be obtained using a common head geometry for a group of patients, for example all adult patients.

4. Inverse Problem for MEG

In embodiments in order to solve the MEG inverse problem we first solve the EEG inverse problem. We assume that the magnetic sensors are oriented radially (though the skilled person will appreciate that this is merely a convenience—for example a radial component of the field may be derived from a sensor at any orientation). We can rewrite equation (5) in the form $$\int_{\Omega_c} \nabla^2 (\tau \cdot A(\tau)) \frac{dV(\tau)}{|r-\tau|} = -\frac{1}{4\pi} \sum_{l \in \{1,2,3\}} \int_{\Omega_c} r_l [\nabla \Psi(\tau) \cdot \nabla_\tau H_l(r, \tau)] dV(\tau) - \frac{4\pi}{\mu} B(r) \cdot r. \quad (51)$$

We assume that an estimate of the function $\hat{\Psi}(\tau)$ has been computed from EEG data, thus all quantities on the right hand side of equation (51) are known. We denote the radial component of the vectorial function $A(\tau)$ by $A^\tau(\tau):=\hat{\tau} \cdot A(\tau)$. A radial basis function expansion of the unknown function $\tau A^\tau(\tau)$ takes the form $$\tau A^\tau(\tau) = \sum_{j=1}^N \beta_j \varphi(\|\tau - \tau_j\|). \quad (52)$$

In order to formulate a least squares problem, we introduce the following notations:

$$M(i, j) = \int_{\Omega_c} \nabla_\tau^2 \varphi(\|\tau - \tau_j\|) \frac{dV(\tau)}{|r_i - \tau|}; r_i \in \Omega_e, \quad (53)$$

$$c(i) = -\frac{1}{4\pi} \sum_{l \in \{1,2,3\}} \int_{\Omega_c} r_{(i,l)} [\nabla \Psi(\tau) \cdot \nabla_\tau H_l(r_i, \tau)] dV(\tau) - \frac{4\pi}{\mu} B(r_i) \cdot r_i.$$

where i denotes the ith sensor index. Then equation (51) yields $$M\beta = c. \quad (54)$$

As in the case of EEG, the employed parametrization acts as an implicit regularization. The MLE estimates yields $$\hat{\beta} = (M^T C_{w'}^{-1} M)^{-1} M^T C_{w'}^{-1} c, \quad (55)$$

where $C_{w'}$ is the covariance matrix of the noise associated with the magnetic field measurement system. The volume integrals of equation (53) are computationally expensive. However, these computations can be parallelized. More precisely, for an arbitrary matrix entry (i, j), the process of solving the volume integral is independent from every other matrix entry. Moreover, for a given geometry, the matrix M defined in equation (53) needs to be computed only once.

Note that in the above care should be taken to distinguish between $c \in \mathbb{R}^+$ (a radial basis function parameter) and $c \in \mathbb{R}^N$ (processed MEG data, where N denotes the number of magnetometers).

Computer Implementation

Referring now to FIG. 1a, this shows a flow diagram of a procedure to numerically implement the solution of the inverse problem for EEG on a computing system. The computing system may either be a general purpose computing system, or a digital signal processor, and/or may comprise dedicated hardware.

At step S100 the procedure inputs the EEG data, represented as a vector b (using the notation of Section 3 above), and at step S102 calculates an estimate of the vector λ by solving b=Eλ by any of many numerical methods which will be well known to those skilled in the art. Once an estimate of λ has been found this can be used to determine an estimate for ψ, from the radial basis functions, which in turn represents the current distribution J. In principle output data from the procedure may be provided in the form of data representing either λ, ψ or J, and/or the current distribution data may be converted into a 3D representation of the EEG data, for example mapped onto a 3D representation of the head and/or brain (cerebrum)—step S114. The skilled person will appreciate that there are many techniques which may be employed to provide a 3D representation of the EEG data, including representing the data as one or more 2D slices.

The procedure of FIG. 1a employs data from the matrix E as previously described, and this may either be calculated or retrieved from storage, as shown in step S101. A procedure for calculating E is described below with reference to FIG. 1c.

FIG. 1b shows a flow diagram of a procedure which may be used to image a current distribution in the brain derived from MEG data. The procedure of FIG. 1b reflects the description in section 4 above. Thus at step S106 the procedure inputs magnetic field data B and, at step S110, determines an estimate of vector β from the equation Mβ=c, again using any one of many techniques which will be well known to those skilled in the art. The matrix M may again either be calculated or retrieved from memory (step S111). In embodiments the procedure calculates the parameter vector c, for example using the head (cerebrum) geometry, the previously calculated approximation for iv, and the previously described vectorial function H. Again H is dependent only on the geometry (internal and external), and conductivity, of the head, and may again be either calculated or retrieved from memory (step S109). Then an estimate of vector β can be determined from Mβ=c.

The procedure then outputs (S112) data representing the vectorial function A, in particular the radial component of this function. This may be determined from a combination of vector β and the radial basis functions (although in principle the output data may comprise β rather than data directly representing A). Then, again, the procedure may generate a 3D representation of the solenoidal part of the current distribution determined from the measured magnetic field B.

Figure 1C:
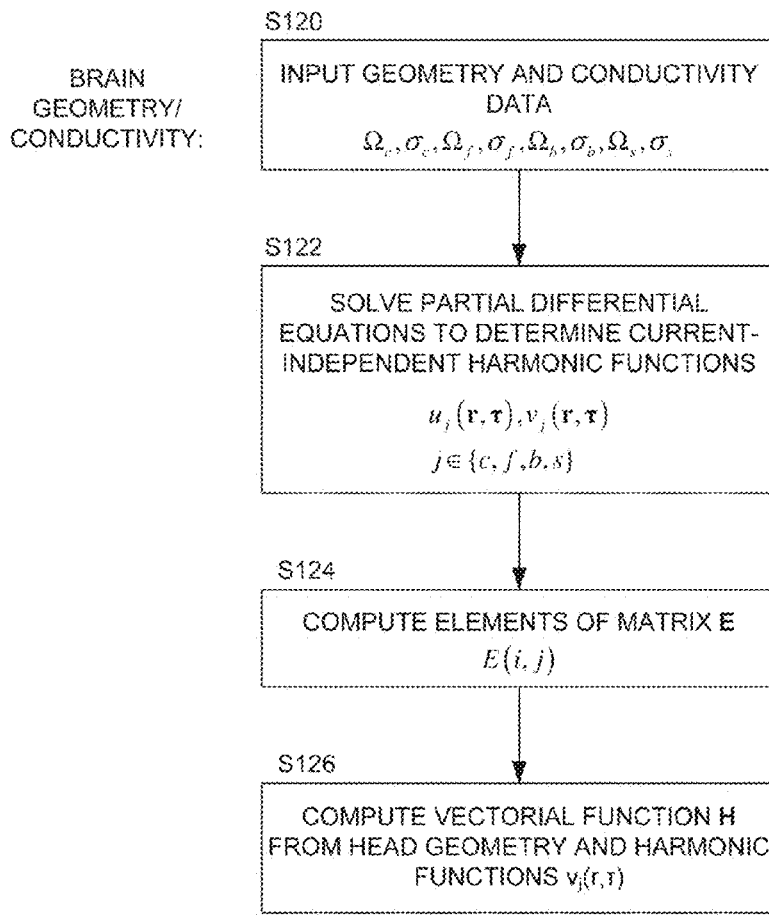

FIG. 1c shows a flow diagram of a procedure for calculating the elements of matrix E and the elements of vectorial function H, by determining current-independent harmonic functions $u_j$ as previously described in Section 2 above. Thus at step S120 the procedure inputs geometry and conductivity data for the head, in particular defining boundaries of the cerebrum, cerebrospinal fluid, bone and scalp, and their respective electrical conductivities. Standard values may be used for the electrical conductivities. The relevant geometry data may be derived, for example, from a magnetic resonance imaging scan of the patient and/or a more generic model may be employed.

At step S122 the procedure solves a set of partial differential equations, as outlined in Section 2 above, to determine the set of current-independent harmonic functions $u_j$ for each of the cerebrum, CSF, bone and scalp. From these the related functions $v_j$ may then be determined (although this step is not essential). The procedure then computes the elements of matrix E (S124), as described in Section 3 above and/or may compute the elements of the vectorial function H as described in Section 4 above. One or both of matrix E and vector function H may then be stored for later use.

Figure 1D:
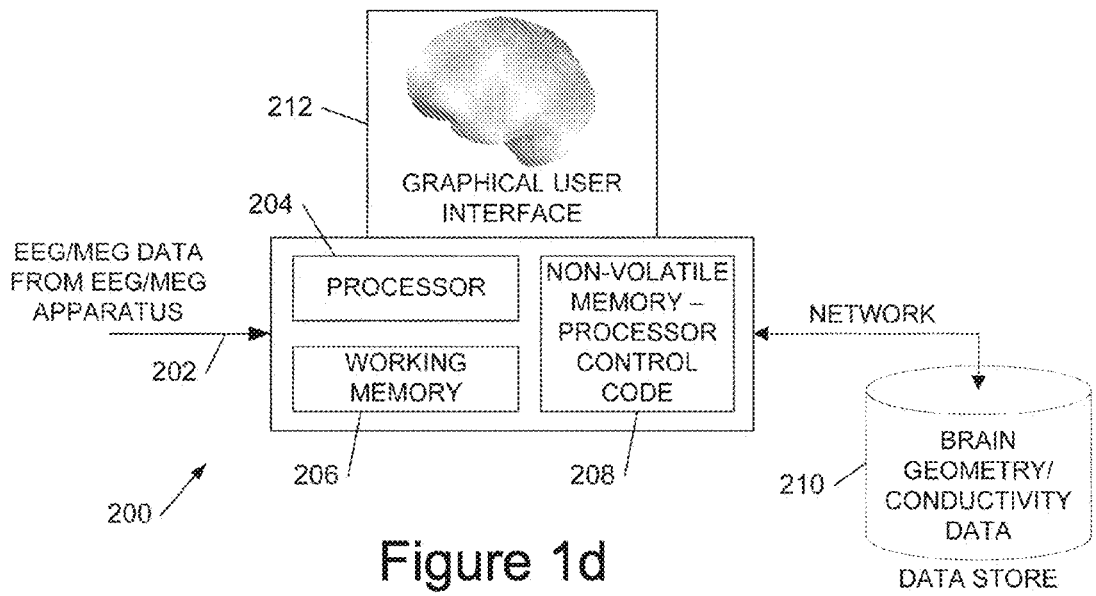

FIG. 1d shows an embodiment of a computer system 200 programmed to implement the methods of FIGS. 1a to 1c. Thus in the illustrated embodiment the computer system comprises a processor 204 coupled to working memory 206 and to non-volatile memory 208 storing processor control code to control the process of 204 to implement the previously described procedures. A graphical use interface 212 is provided for displaying a 3D representation of the determined current distribution(s) to the user, although the skilled person will appreciate that additionally or alternatively other forms of storage/output may be employed. The computer system 200 has an input 202 from EEG and/or MEG apparatus; this may, for example, comprise a connection over a computer network. In a similar manner the computer system 200 has access to a data store 210, again optionally over a computer network. The optional but preferable data store 210 may be employed to store one, some or all of the parameters described with reference to FIG. 1c for use in solving the inverse problem for EEG and/or MEG, in particular brain geometry/conductivity data. Optionally a pre-computed inverse matrix for EEG and/or MEG may be stored or, for example, a pre-computed inverse matrix for each of a number of topologies may be provided as a library, for example indexed by user.

Although an example embodiment has been described which employs a general purpose computing system, the skilled person will appreciate from the foregoing discussion that the final 'imaging' step reduces to a matrix by vector multiplication (the matrix inverse may be pre-computed). Thus it will be appreciated that once the procedure of FIG.

1c has been run, the remaining processing load is small and may be run in, say, a dedicated application specific integrated circuit (ASIC) and/or on a mobile device such as a tablet computer or smart phone. A data store storing the pre-computed inverse matrix may be at a remote location accessible (with suitable security) via a wired or wireless network.

5. A Numerical Estimate of $v_s(r,\tau)$, and $\nabla_\tau H(r,\tau)$

The preceding approach was validated by performing a forward calculation and checking that the solution to the inverse problem agreed with the initial data. In this section we compare the analytic expression for $v_s(r,\tau)$ obtained from equation (24) with a numerical estimate obtained via the approach outlined in section 2.2. We take the following values for the radii, and the conductivities:

| $r_c$ = 0.071m | $r_f$ = 0.074m | $r_b$ = 0.079m | $r_s$ = 0.085m |
|---|---|---|---|
| $\sigma_c$ = 0.33 | $\sigma_f$ = 1 | $\sigma_b$ = 0.0125 | $\sigma_s$ = 0.33 |

For the source, we let $\tau$=[0.0226, 0.0068, 0.0258]m, Q=[1,1,1]/$\sqrt{3}$. We use a numerical implementation based on a boundary element method as outlined in Z. Akalin-Akar ibid. We compute $u_s(r,\tau)$ at 1026 discrete points on the outer surface r=0.085 m. The results for a 256 point subset of arbitrary discrete points on the outer surface are presented in FIG. 2a. The circles show the analytic solution, and the solid line with dots is the solution from the boundary element method. The small discrepancy between the numerical and the analytic solution varies between numerical solvers, and it depends on several factors including the mesh, element types, the numerical integration, and specific assumptions used in the implementation. The comparison of the analytical solution for $v_s(r,\tau)$ for a 256 point subset on the outer surface is shown in FIG. 2b. The circles show the analytical solution given by equation (24); the solid line with dots is the numerical solution outlined in section 2.2 above.

The inverse MEG formulation relies on the complete solution of the boundary value problem described by equations (10)-(13). We consider the multi-layer spherical geometry described below:

| $r_c$ = 0.071m | $r_f$ = 0.074m | $r_b$ = 0.079m | $r_s$ = 0.085m |
|---|---|---|---|
| $\sigma_c$ = 0.33 | $\sigma_f$ = 1 | $\sigma_b$ = 0.0125 | $\sigma_s$ = 0.33 |

We present a solution for a finite set of observation points, and an arbitrary source point. We introduce the following notation:

$$\partial\Omega_i^\pm := \partial\Omega_i \pm \gamma\hat{n}_i\; i\in c,f,b$$

where $\hat{n}$ is a unit vector normal to the surface $\partial\Omega_i$. In our numerical tests we set $\gamma=10^{-3}$. This corresponds to a small movement towards inside ($-\gamma$) and outside ($+\gamma$) of the domain $\Omega_i$. We solve $v_c(r,\tau)$ on the surface $\partial\Omega_c^-$, and $v_f(r,\tau)$ on the surface $\partial\Omega_c^+$. For the surface $\partial\Omega_f$, we solve $v_f(r,\tau)$ on the surface $\partial\Omega_f^-$, and $v_b(r,\tau)$ on the surface $\partial\Omega_f^+$. For the surface $\partial\Omega_b$, we solve $v_b(r,\tau)$ on the surface $\partial\Omega_b^-$, and $v_s(r,\tau)$ on the surface $\partial\Omega_b^+$. For the surface $\partial\Omega_s$, we present the analytical and numerical solution of the function $v_s(r,\tau)$ in FIG. 3. We consider an arbitrary source point $\tau$=[0.0226, 0.0068, 0.0258]m and 140 arbitrary discrete observation points r on each surface. It is clear that the solution at the observation points on surfaces closer to the source point $\tau\in\Omega_c$, namely $\partial\Omega_i^-$, have a slightly larger amplitude than the solution on surfaces $\partial\Omega_i^+$. The solutions converge as $\gamma\rightarrow 0$.

Figure 2A:
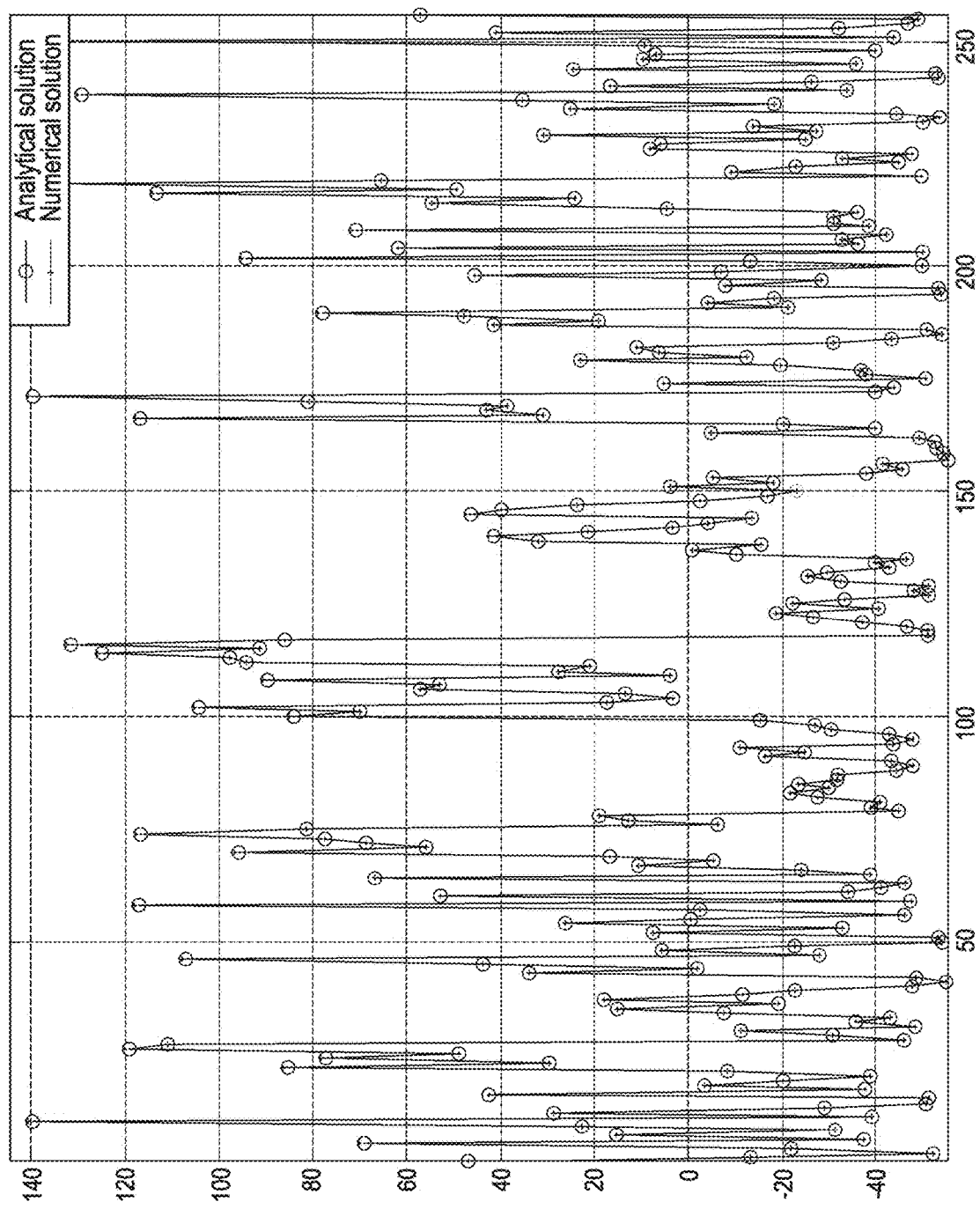
FIGS. 2a and 2b show a comparison of analytical solution and numerical solutions for $u_s(r,\tau)$ and for $v_s(r,\tau)$ respectively.
Figure 2B:
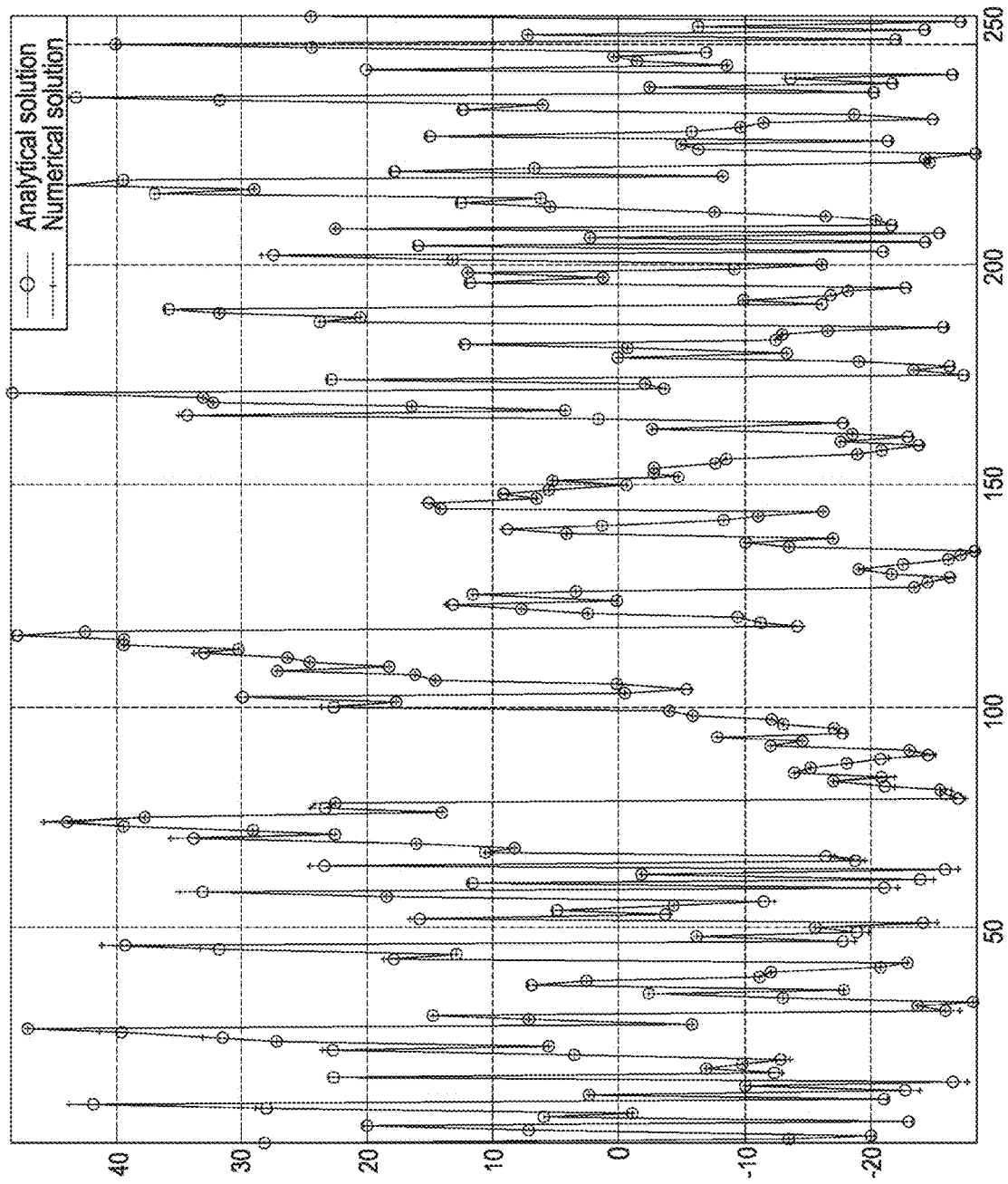

FIG. 2a shows a comparison of the analytical solution and of a numerical solution of $u_s(r,\tau)$ which is described by equations (15)-(18). The radii are [0.071, 0.074, 0.079, 0.085]m, and the corresponding conductivities are [0.33, 1, 0.0125, 0.33]. A dipole described by $\tau$=[0.0226, 0.0068, 0.0258]m, Q=[1,1,1]/$\sqrt{3}$ is used as a source. The line with circles is the analytical solution and the solid dot line is a numerical solution.

FIG. 2b shows a comparison of the analytical solution and of a numerical solution of $v_s(r,\tau)$ which is described by equations (10)-(13). The line with circles is the analytical solution, equation (24), and the solid line with dots is the solution using the approach outlined in section 2.2 above. The radii are [0.071, 0.074, 0.079, 0.085]m, and the corresponding conductivities are [0.33, 1, 0.0125, 0.33]. A source position has been fixed at $\tau$=[0.0226, 0.0068, 0.0258]m. A total of 256 arbitrary points have been selected on the outer surface.

Figure 3:
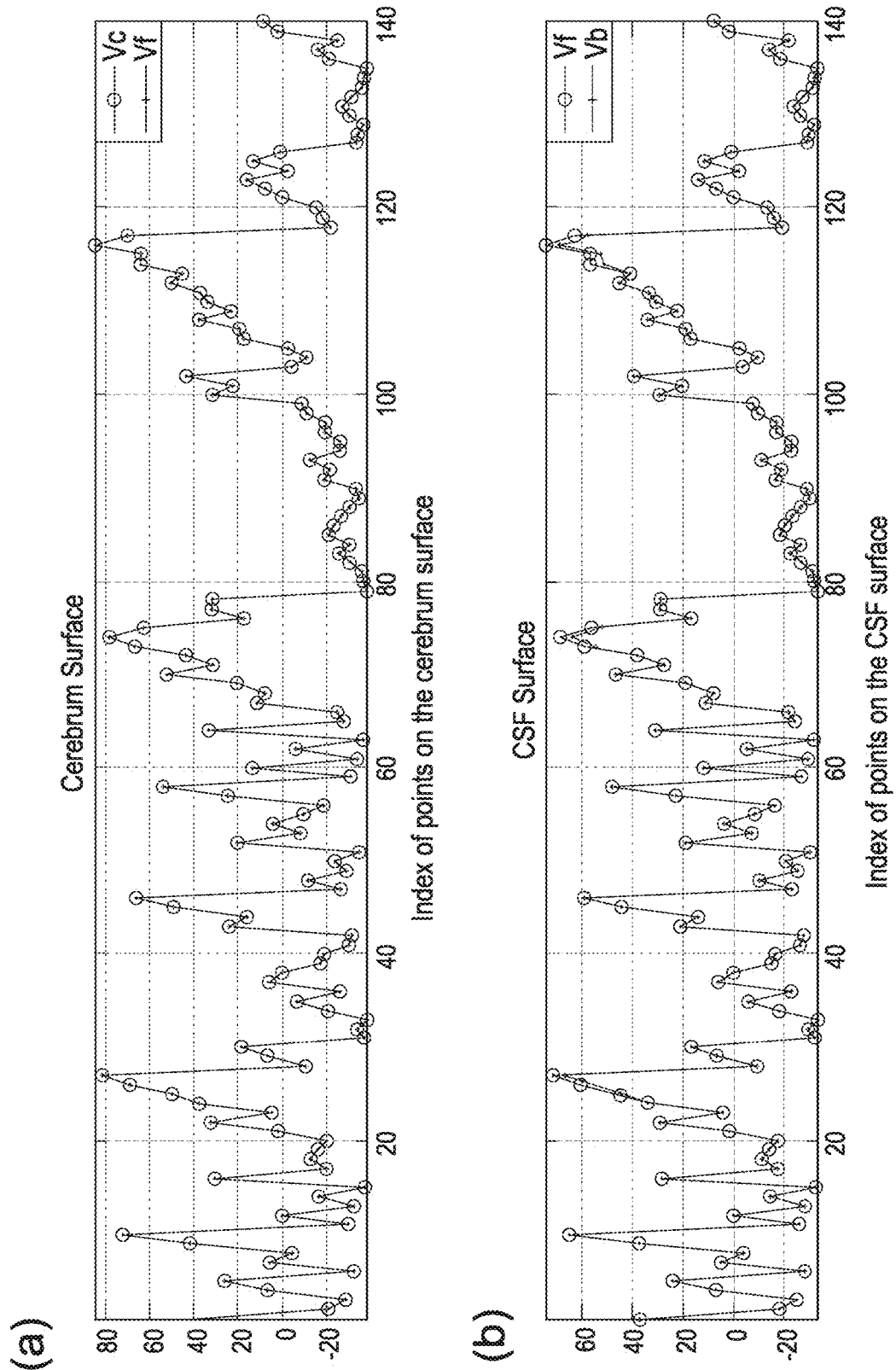
FIG. 3 illustrates solutions of a boundary value problem for a multi-layer spherical geometry.
Figure 3:
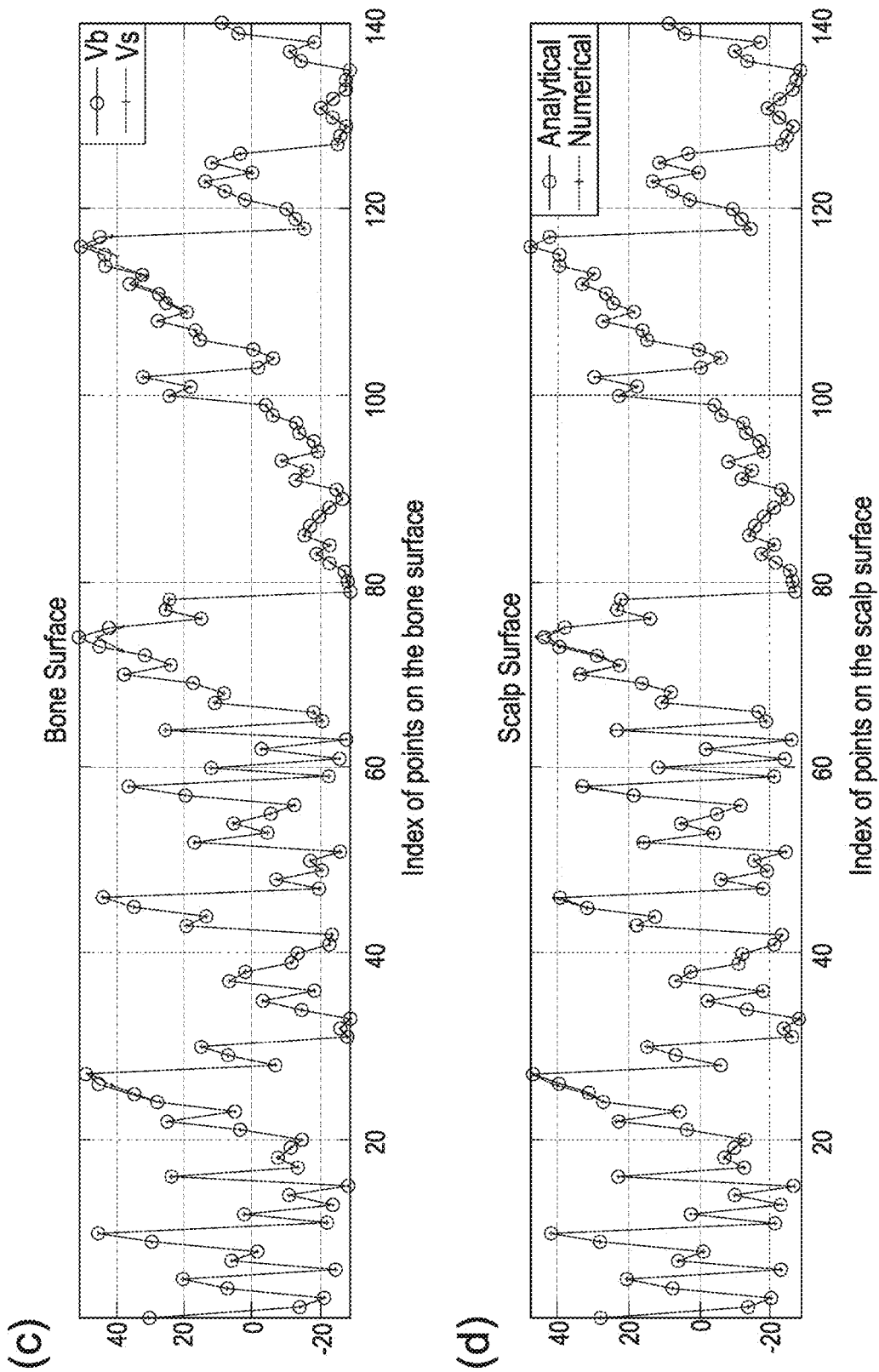

FIG. 3 shows the solution of the boundary value problem described by equations (10)-(13) for every surface of the multi-layer spherical geometry. The radii are [0.071, 0.074, 0.079, 0.085]m, and the corresponding conductivities are [0.33, 1, 0.0125, 0.33]. A source position has been fixed at $\tau$=[0.0226, 0.0068, 0.0258]m. For every surface, 140 arbitrary points have been selected. FIG. 3a shows $v_c(r,\tau)$ and $v_f(r,\tau)$ on the surface $\partial\Omega_c$. FIG. 3b shows $v_f(r,\tau)$ and $v_b(r,\tau)$ on the surface $\partial\Omega_f$. FIG. 3c shows $v_b(r,\tau)$ and $v_b(r,\tau)$ on the surface $\partial\Omega_b$. FIG. 3d shows the analytical and numerical solution of $v_b(r,\tau)$ on the surface $\partial\Omega_s$.

Figure 4:
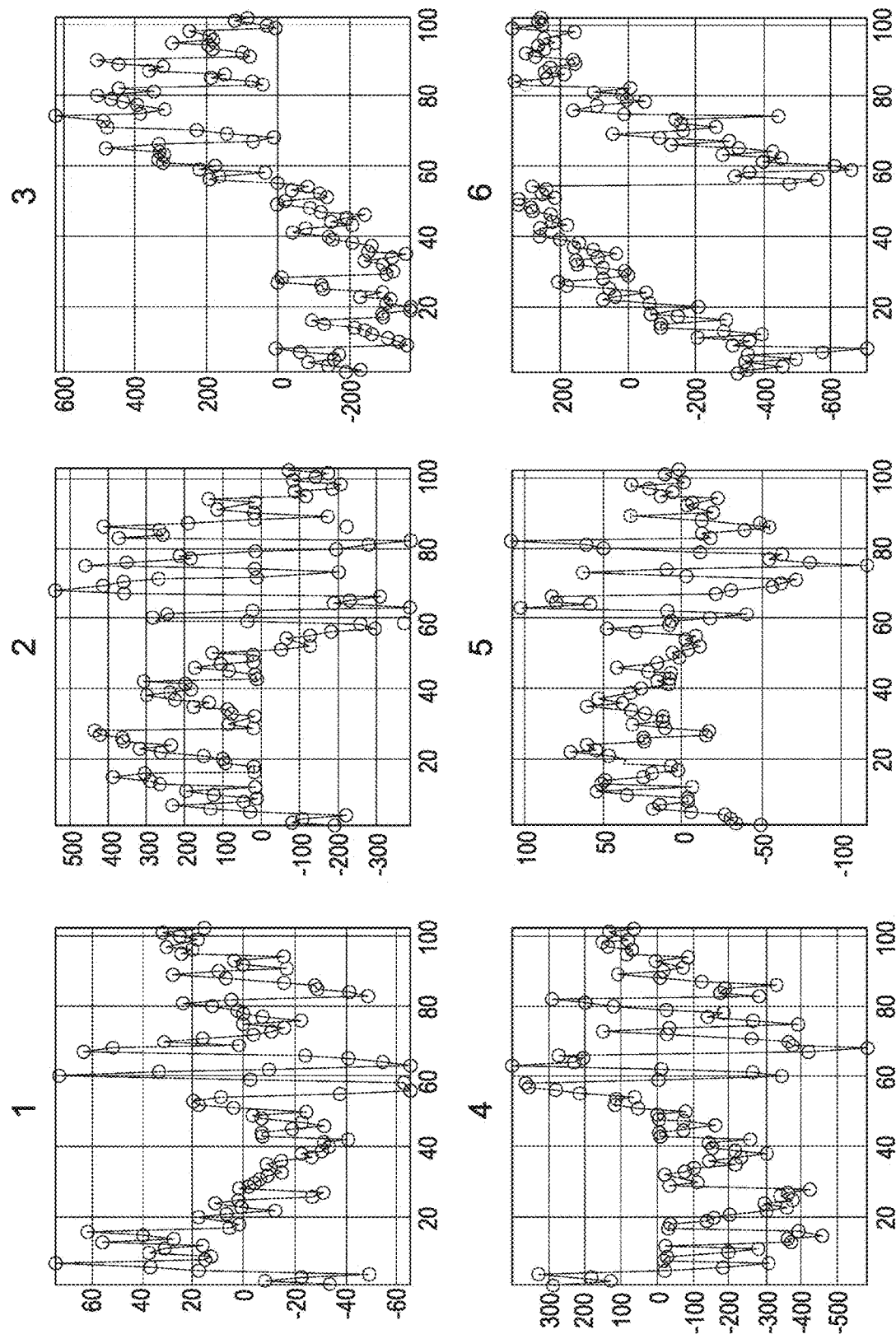
FIG. 4 illustrates elements of a matrix $\nabla_r H(r,\tau)$ problem for a multi-layer spherical geometry.
Figure 4:
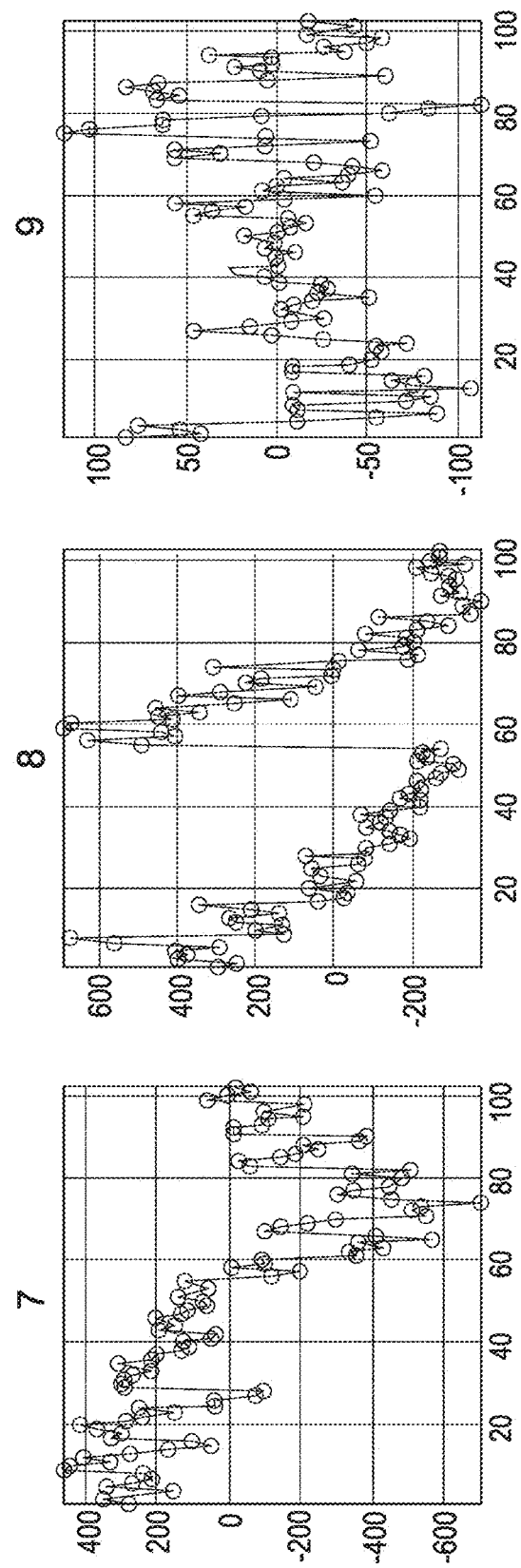

FIG. 4 shows the elements of the matrix $\nabla_\tau H(r,\tau)$ given by equation (39) for the multi-layer spherical geometry. The radii are [0.071, 0.074, 0.079, 0.085]m, and the corresponding conductivities are [0.33, 1, 0.0125, 0.33]. A source position has been fixed at $\tau$=[-0.0397, -0.0284, 0.0057]m. On the subfigures, the x-axis values are sensor indexes and the y axis shows the functions $$\frac{\partial H_j}{\partial \tau_i}.$$

The solid line with circles is the analytical solution and the solid line with dots is the numerical solution. Each of the nine functions is identified by a numerical header. They are as follows:

$$\frac{\partial H_1}{\partial \tau_1}, \quad (1)$$

$$\frac{\partial H_1}{\partial \tau_2}, \quad (2)$$

$$\frac{\partial H_1}{\partial \tau_3}, \quad (3)$$

$$\frac{\partial H_2}{\partial \tau_1}, \quad (4)$$

$$\frac{\partial H_2}{\partial \tau_2}, \quad (5)$$

$$\frac{\partial H_2}{\partial \tau_3}, \quad (6)$$

-continued $$\frac{\partial H_3}{\partial \tau_1}, \quad (7)$$

$$\frac{\partial H_3}{\partial \tau_2}, \quad (8)$$

$$\frac{\partial H_3}{\partial \tau_3}. \quad (9)$$

The results of FIGS. 2-4 demonstrate that the previously described approach provides an accurate numerical solution to the inverse problem.

6. Numerical Result: Three Layer Head Model

Figure 5A:
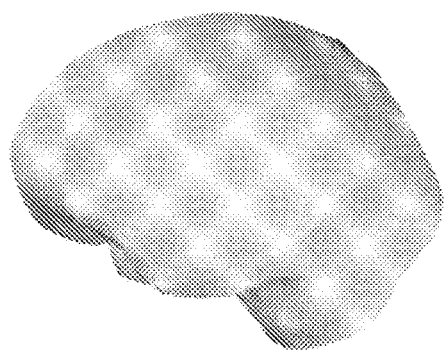
FIGS. 5a to 5c show, respectively, the cerebrum, $\Omega_c$, the skull, $\Omega_b$, and the head, $\Omega_s$ of a three layer realistic head model.
Figure 5B:
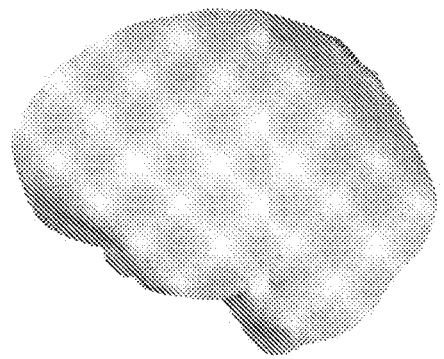
Figure 5C:
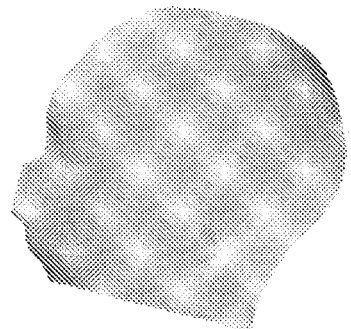

In the case of the three layer realistic head model, we have 86 electrodes. We consider a radial basis function expansion with 75 coefficients. The head geometry is shown in FIG. 5. Thus FIG. 5 shows the three layer realistic head model used for the results described herein. In more detail, FIGS. 5a to 5c show, respectively, the cerebrum, $\Omega_c$, the skull, $\Omega_b$, and the head, $\Omega_s$. The BEM (boundary element method) discretization involves a total of 2476 vertices and 4940 triangles.

6.1 Numerical Estimate of the Current Via EEG

We consider the synthetic function $\Psi(\tau)$ defined by $$\Psi(\tau) = \sum_{l=1}^{L} \sum_{i=1}^{2} k_i h_i^l \left( \frac{1}{l} - \ln\left[\frac{\tau}{c_1}\right] \right) c_1^{2l+1} \frac{(2l+1)^2}{4\pi} P_l(\eta_i \cdot \hat{\tau}) \quad (56)$$

We set L=50 and use the following values:

$$h_1 = 0.3, \eta_1 = \left[\frac{1}{\sqrt{3}}, \frac{1}{\sqrt{3}}, \frac{1}{\sqrt{3}}\right], k_1 = 0.029,$$

$$h_2 = 0.4, \eta_2 = \left[\frac{1}{\sqrt{2}}, 0, -\frac{1}{\sqrt{2}}\right], k_2 = 0.015.$$

Figure 6:
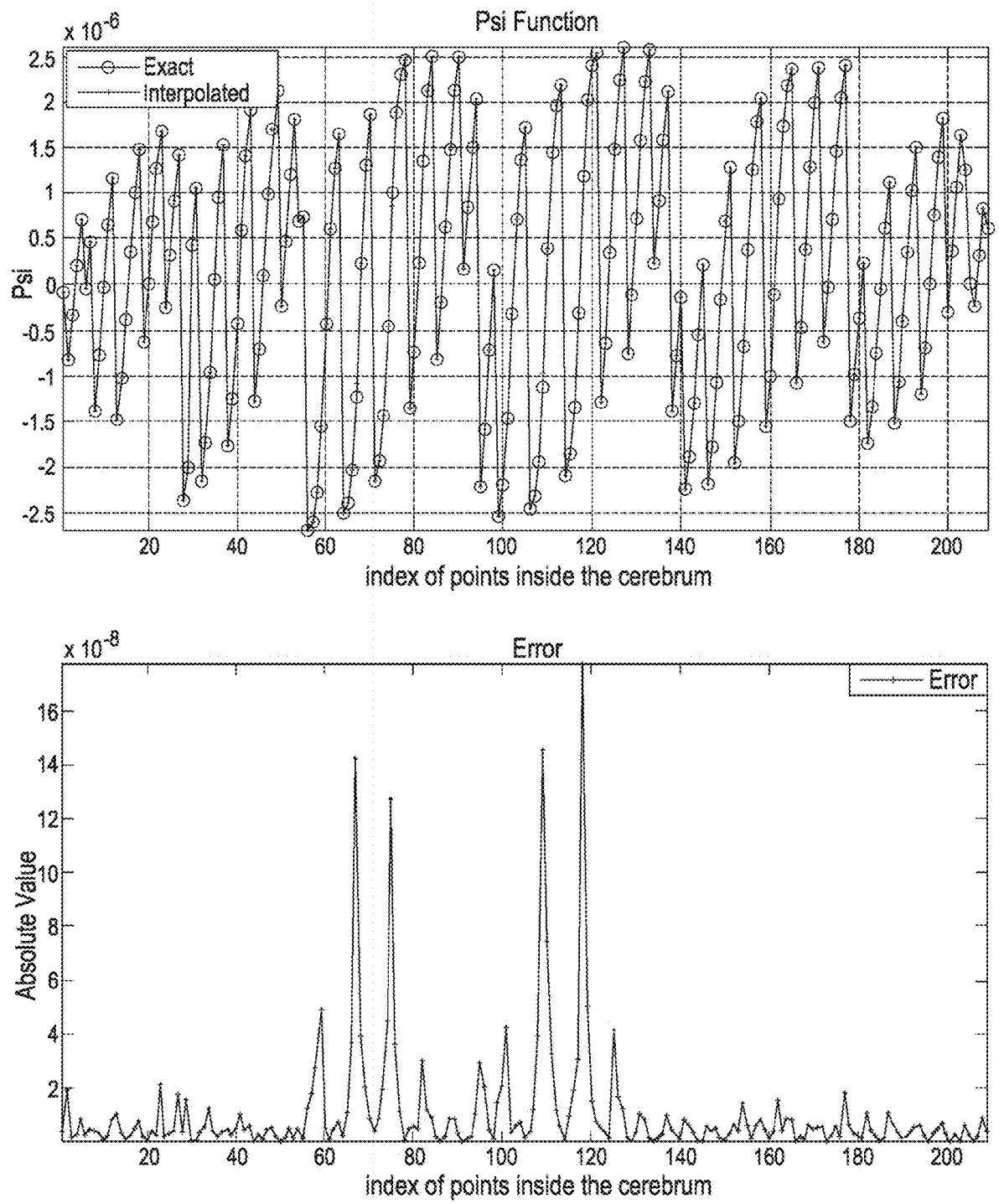
FIG. 6 shows values of a synthetic function $\Psi(\tau)$ inside the cerebrum of the three layer head model of FIG. 5.

We consider a radial basis function (RBF) expansion of the function $\Psi(\tau)$. All information about the function $\Psi(\tau)$ is encoded into the parametrization $\{(\lambda_j, \tau_j): 1 \leq j \leq N, \varphi(r) = (r^2 + c^2)^{1/2}\}$. The parameters of interest are the components of the vector $\lambda$. In order to avoid the "inverse crime", we choose a different discretization of equation (4) to generate the synthetic data than the one used to perform the reconstruction. The RBF expansion of the function (56) is shown in FIG. 6. We have used 75 equally spaced points in the cerebrum, i.e N=75 in equation (47). It is clear from FIG. 6 that this expansion is sufficiently accurate to represent the synthetic function $\Psi(\tau)$. We assume a signal to noise ratio (SNR) of 20 dB, and model the noise as white Gaussian noise i.e $w \sim N(0, \sigma^2 I)$. The reconstructions are shown in FIG. 7.

Thus FIG. 6 shows the RBF (radial basis function) expansion of the function (6.1), showing the synthetic function $\Psi(\tau)$ and the corresponding radial basis function interpolation of $\Psi(\tau)$ inside the domain $\Omega_c$ of the three layer head model. We used 75 coefficients and sampled the function on a Cartesian grid inside the domain $\Omega_c$. The top figure shows the function $\Psi(\tau)$ defined by equation (56) as well as the corresponding radial basis function interpolation. The bottom figure shows the absolute error between the exact $\Psi(\tau)$ and the corresponding interpolation.

Figure 7:
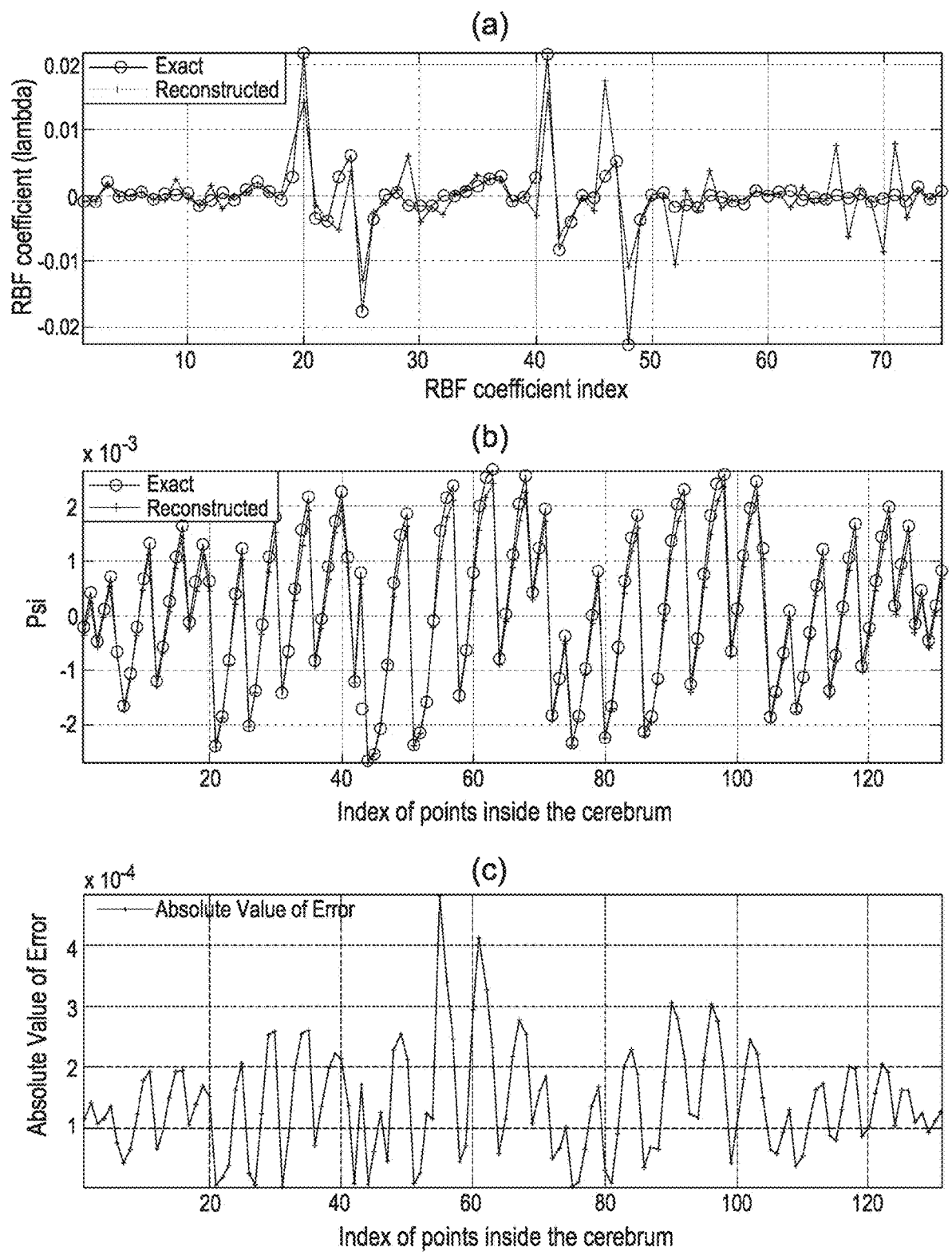
FIG. 7 shows exact and reconstructed functions $\Psi(\tau)$ for the three layer head model of FIG. 5.

FIG. 7 shows the exact and reconstructed functions $\Psi(\tau)$ for the three Layer head model. We have used 75 coefficients and 86 electrodes. The signal to noise ratio (SNR) is 20 dB. In FIG. 7a, the solid line with circles shows the exact $\lambda$, equation (47), whereas the solid line with dots is the reconstructed $\hat{\lambda}$, equation (50). In FIG. 7b, the solid line with circles is $\Psi(\tau)$ as given by equation (56), whereas the solid line with dots is the reconstructed current computed using the estimated $\hat{\lambda}$. FIG. 7c shows the error $e(\tau) := |\Psi(\tau) - \hat{\Psi}(\tau)|$ of the functions shown in FIG. 7b.

6.2 Numerical Estimate of the Current Via MEG

We consider the synthetic function used in Fokas, *Inverse Problems*, ibid, to represent $\tau A^{\tau}(\tau)$, but with different numerical values. The function $\tau A^{\tau}(\tau)$ is given by $$\tau A^\tau(\tau) = \sum_{i=1}^{2} k_i \left[ \frac{1}{4\pi} \frac{1 - h_i^2}{(1 + h_i^2 - 2h_i(\eta_i \cdot \hat{\tau}))^{1.5}} - \frac{1}{4\pi} \right]. \quad (57)$$

We use the following values:

$$h_1 = 0.3, \eta_1 = \left[\frac{1}{\sqrt{3}}, \frac{1}{\sqrt{3}}, \frac{1}{\sqrt{3}}\right], k_1 = 0.029,$$

$$h_2 = 0.4, \eta_2 = \left[\frac{1}{\sqrt{2}}, 0, -\frac{1}{\sqrt{2}}\right], k_2 = 0.0047.$$

Figure 8:
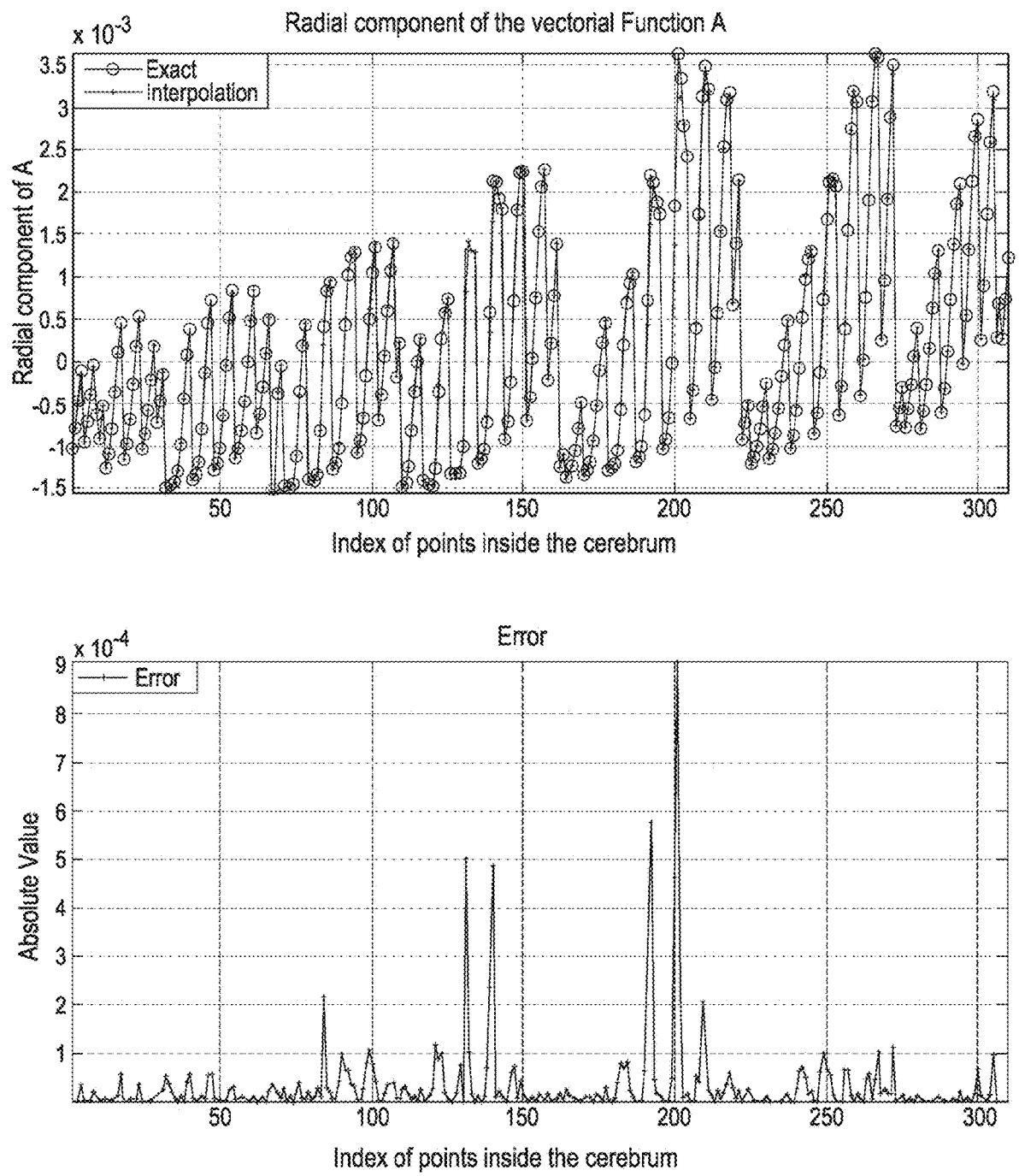
FIG. 8 shows values of a synthetic function $\tau A^\tau (\tau)$ inside the cerebrum of the three layer head model of FIG. 5.

As in the case with EEG, we employ a RBF expansion for the function $\tau A^{\tau}(\tau)$. All information about the function $\tau A\tau(\tau)$ is encoded into the parametrization $\{(\beta_j, \tau_j): 1 \leq j \leq N, \varphi(r) = (r^2 + c^2)^{1/2}\}$. The parameters of interest are the components of the vector $\beta$. In order to avoid the "inverse crime" we choose a different discretization of equation (5) to generate the synthetic data than the one used to perform the reconstruction. The RBF expansion of the function (57) is shown in FIG. 8. We used 75 equally spaced points in the cerebrum, i.e N=75 in equation (52). It is clear from FIG. 8 that this expansion is sufficiently accurate to represent the synthetic function $\tau A^{\tau}(\tau)$. We assume a signal to noise ratio (SNR) of 20 dB and model the noise as white Gaussian noise i.e $w' \sim N(0, \sigma^2 I)$. We have 102 real sensor positions to obtain the measurements. The reconstructions are shown in FIG. 9.

Thus FIG. 8 shows the synthetic function $\tau A^{\tau}(\tau)$ and the corresponding radial basis function interpolation of $\tau A^{\tau}(\tau)$ inside the domain $\Omega_c$ of the three layer head model. We used 75 coefficients and sampled the function on a Cartesian grid inside the domain $\Omega_c$. The top figure shows the function $\tau A^{96}(\tau)$ as given by equation (57), as well as the corresponding radial basis function interpolation. The bottom figure shows the absolute error between the exact $\tau A^{\tau}(\tau)$ and the corresponding interpolation.

Figure 9:
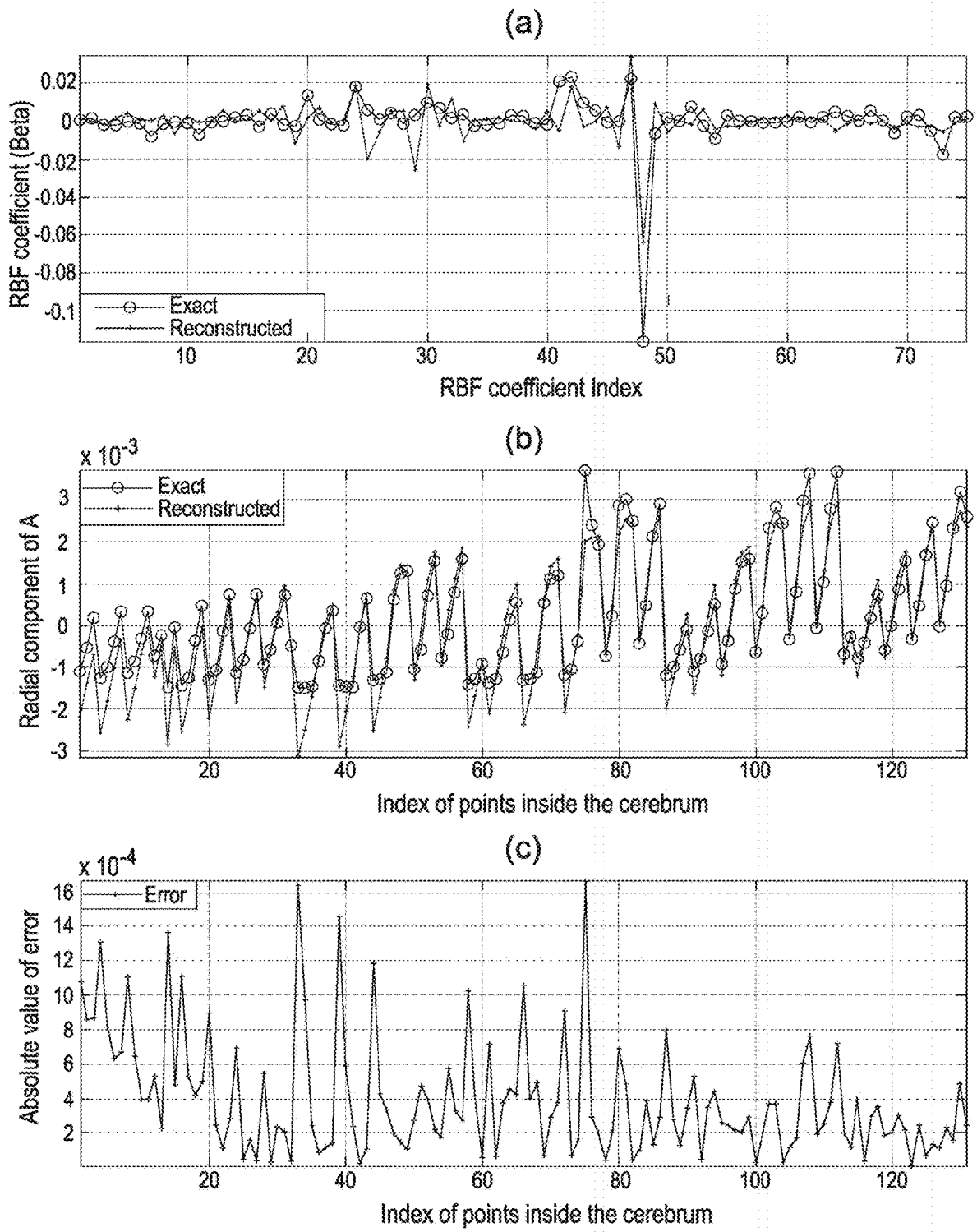
FIG. 9 shows exact and reconstructed functions $\tau A^\tau (\tau)$ for the three layer head model of FIG. 5.

FIG. 9 shows the exact and reconstructed $\tau A^{\tau}(\tau)$ and the three layer head model. We used 75 coefficients and 102 real sensor positions. The signal to noise ratio (SNR) is 20 dB. In FIG. 9a, the solid line with circles shows the exact $\beta$, equation (52), whereas the solid line with dots is the reconstructed $\hat{\beta}$ as given by equation (57). In FIG. 9b, the solid line with circles is $\tau A^{\tau}(\tau)$ as given by equation (57), whereas the solid line with dots is the reconstructed current computed using the estimated $\hat{\beta}$. FIG. 9c shows the error $e(\tau) := |\tau A^{\tau}(\tau) - \tau \hat{A}^{\tau}(\tau)|$ of the functions shown in FIG. 9b.

7. Conclusion

We have introduced an algorithmic approach for extracting the maximum possible information about the neuronal current $J^P(\tau)$, $\tau \in \Omega_c$, from the measurement of the electric potential $u_s(r)$, $r \in \partial\Omega_s$, on the scalp, and from the measurement of the radial part of the magnetic field $r \cdot B(r)$ $r \in \Omega_e$ in the exterior of the head, relying on a numerical approach for computing the auxiliary functions $\nabla_\tau v_s(r,\tau)$ and $\nabla_\tau H(r,\tau)$. In section 2.1 we derived analytic expressions for $v_s(r,\tau)$ and $\nabla_\tau H(r,\tau)$ for the particular case of the spherical geometry. This allowed us to verify the effectiveness of the above numerical codes; the agreement with the analytical expressions is excellent. In section 6 we implemented our general approach to a realistic three shell geometry. The above algorithm yields accurate reconstructions both for the component $\Psi(\tau)$ of the current from the data set $\{u_s(r_i): 1 \leq i \leq N_e\}$, as well as for the radial component of the vectorial function $A(\tau)$ (denoted by $\tau A^\tau(\tau)$) from the data set $\{r_k \cdot B(r_k): 1 \leq i \leq N_s, r_k \in \Omega_e\}$ and the estimated function $\Psi(\tau)$. Indeed, starting with the particular function $\Psi(\tau)$ given by equation (56), we generate a set of synthetic data for the electric potential on the scalp; using this set we show that we can reconstruct the function $\Psi(\tau)$ even in the presence of noise. Similarly, starting with the functions $\Psi(\tau)$ and $\tau A^\tau(\tau)$ given by equations (56) and (57) respectively, we generate a set of synthetic data for the radial part of the magnetic field outside the head; then, using this set as well as the reconstructed function $\Psi(\tau)$, we show that we can reconstruct the radial part of $A(\tau)$ even in the presence of noise. The assumed noise model in both the EEG and MEG is additive white Gaussian with a signal to noise ratio of 20 dB.

It can thus be seen that embodiments of the above described algorithm are well-suited to address the distributed source problem, in particular in real time, and can handle reasonable noise levels in the measurements.

EEG can yield as much information about the neuronal current as MEG, but at a fraction of the cost since EEG devices are inexpensive and widely available. A further advantage of EEG (and MEG) by comparison with other techniques such as fMRI, PET and the like is the fast time resolution—EEG and MEG can make 10s or 100s of measurements per millisecond. Furthermore, it is straightforward to reconstruct images of the current distributions from EEG data and MRI data (for the head geometry).

Thus a further aspect of the invention contemplates an upgrade for a patient imaging machine, such as a magnetic resonance imaging machine, provided by combining the machine with EEG (and/or MEG) signal measurement apparatus and EEG (and/or MEG) signal processing software or hardware as described above. Such an upgrade may be of substantial benefit in diagnosis and treatment of many neurological diseases including, for example, epilepsy. In another application such an approach may be employed to differentiate 'mild cognitive impairment' (a transitional stage between normal aging and Alzheimer's disease) from Alzheimer's disease proper.

EEG technology is also finding its way into the consumer market—for example low cost EEG headsets are becoming available for games. Thus a further application of the embodiments of the invention uses processing as described above to provide data for performing an action and/or controlling a consumer electronic device, for example for controlling a computer game or the like. More generally, embodiments of the techniques we describe may be employed to detect a user's thoughts and/or feelings and/or expressions in real time.

The skilled person will appreciate that numerous variations of the above described techniques are possible. For example, although we have described the use of radial basis functions for expanding the neuronal current other basis functions may also be used. Either or both of the inverse EEG and inverse MEG algorithms may be partially, or substantially wholly, parallelised.

Optionally Bayesian filtering and/or dynamic parameter estimation or other time series analysis may be applied to either or both of the raw data and processed data. The skilled person will appreciate that the EEG and/or MEG signals used may be pre-processed in many different ways, for example by filtering to attenuate noise, using any of a range of techniques. Similarly there are many different ways in which a graphical user interface may be provided to operators of the system, for example to facilitate a user in conducting a real-time experiment. Against the skilled person will appreciate that there are many ways in which data from the procedures we have described may be post-processed.

No doubt many other effective alternatives will occur to the skilled person. It will be understood that the invention is not limited to the described embodiments and encompasses modifications apparent to those skilled in the art lying within the spirit and scope of the claims appended hereto.

The invention claimed is:

1. A method of processing an EEG and/or MEG signal to generate image data representing a 3D current distribution, J, within the brain, the method comprising:
   capturing a plurality of electric and/or magnetic measurements from the exterior of the head;
   solving an integral equation for a part of said current distribution to generate said image data representing said 3D current distribution, wherein said integral equation comprises an integral of a first function representing said part of said current distribution and of a second function ($\nabla_\tau v_s(r,\tau)$) representing the geometry and conductivity of the head independent of said current distribution;
   wherein said solving comprises:
   modelling the head as at least two regions separated by at least one internal boundary, and
   solving a set of partial differential equations, one for each said internal region, each partial differential equation comprising a geometry-conductivity function ($w(r,\tau)$) representing the geometry and conductivity of the respective region, wherein said solving is subject to a boundary condition that either i) the gradients of the functions across the or each said internal boundary are smooth when conductivity is taken into account, or ii) a normal component of the electric field of said part of said current distribution is continuous across the or each said internal boundary, and wherein said geometry-conductivity function for an outermost said region of said head defines said second function ($\nabla_\tau v_s(r,\tau)$).

2. A method as claimed in claim 1 wherein said set of partial differential equations comprise a set of partial differential equations dependent said geometry and conductivity of the respective regions and independent of said 3D current distribution, each representing the effect of geometry and conductivity on an electric field in the region from the next inner region, and wherein the electric field in an innermost said region comprises a field generated by a monopole source.

3. A method as claimed in claim 2 wherein said innermost region contains said 3D current distribution and wherein a partial differential equation for said innermost said region is non-Laplacian.

4. A method as claimed in claim 1, wherein said set of partial differential equations comprises a partial differential equation for an innermost said region in the form:

$$\sigma_c \nabla^2 w_c \propto \nabla \cdot Q\delta(r-\tau)$$

where r is a position vector within said innermost region, τ is a dummy variable, Q is a charge, δ is the delta function, $w_c$ is the geometry-conductivity function for said innermost region and $\sigma_c$ is an electrical conductivity of said innermost region; and wherein one or more partial differential equations for subsequent successively more outer regions j have the form:

$$\nabla^2 w_j = 0.$$

5. A method as claimed in claim 4 wherein said boundary conditions define that $$\sigma_{j-1} \frac{\partial w_{j-1}}{\partial n} = \sigma_j \frac{\partial w_j}{\partial n}$$

where j−1 denotes a region within region j, and where n denotes a unit vector outward normal to the surface of the boundary between regions j−1 and j.

6. A method as claimed in claim 1 wherein said geometry-conductivity function for said outermost region of said head, $w_s(r,\tau)$, defines said second function ($\nabla_\tau v_s(r,\tau)$) through the relationship that $w_s(r,\tau)$ is proportional to said second function ($w_s(r,\tau) \propto \nabla_\tau v_s(r,\tau)$).

7. A method as claimed in claim 1 wherein said integral equation comprises one or both of:

$$u_s(r) = -\frac{1}{4\pi} \int_{\Omega_c} (\nabla^2 \Psi(\tau)) v_s(r, \tau) dV(\tau), r \in \partial\Omega_s,$$

or an equation derivable therefrom, where $u_s(r)$ defines measured electric potential on a boundary of said outermost region of the head [the scalp] at position r, $\Omega_c$ defines an innermost said region, $\Omega_s$ defines a surface of said outermost region of the head, $v_s(r,\tau)$ is an integral of said second geometry-conductivity function $\nabla_\tau v_s(r,\tau)$ for said outermost region of said head, and ψ is a scalar value representing an irrotational part of said 3D current distribution; and $$\frac{4\pi}{\mu} B(r) \cdot r = -\int_{\Omega_c} \nabla^2 (\tau \cdot A(\tau)) \frac{dV(\tau)}{|r-\tau|} + \frac{1}{4\pi} \int_{\Omega_c} (\nabla^2 \Psi(\tau)) r \cdot H(r, \tau) dV(\tau) \; r \in \Omega_e,$$

or an equation derivable therefrom, where B(r) defines a measured magnetic field at a sensor position r, $\Omega_c$ defines said innermost region of the head, and $\Omega_e$ defines an external region beyond said outermost said region of said head, H(r,τ) is a vectorial geometry-conductivity function for said head defined by said geometry-conductivity functions for said regions of said head (w(r,τ)), ψ is a scalar value representing an irrotational part of said 3D current distribution and τ·A(τ) defines a radial component of a solenoidal part of said 3D current distribution.

8. A method as claimed in claim 1 further comprising determining a scalar value, ψ, representing an irrotational part of said 3D current distribution, J, from said plurality of electric and/or magnetic measurements.

9. A method as claimed in claim 8 wherein said determining of said scalar value, ψ, uses an expansion of ψ in terms of expansion basis functions having respective unknown coefficients defined by a vector λ, where b=E·λ, where b comprises a vector representation of said measurements of electric potential, $b(r_i)$ at positions $r_i$, and where elements E(i,j) of matrix E are defined by a combination of a jth respective basis function and said geometry-conductivity function for said outermost region of said head, $w_s(r,\tau)$ at position $r_i$, wherein E represents the geometry and conductivity of the head independent of said current distribution, the method comprising determining an estimate of said unknown coefficients, λ, for a solution of b=E·λ, to determine said representation of ψ.

10. A method as claimed in claim 8 wherein said EEG/MEG signal is an EEG signal, wherein said plurality of electric and/or magnetic measurements comprises a plurality of measurements of electric potential on the scalp (b), and wherein said image data includes a representation of ψ.

11. A method as claimed in claim 1 wherein said EEG/MEG signal comprises an MEG signal, the method comprising determining a radial component of a solenoidal part of said 3D current distribution, and wherein said image data comprises a representation of said radial component of a solenoidal part of said 3D current distribution.

12. A method as claimed in claim 11 wherein said determining of said radial component of said solenoidal part of said 3D current distribution, τ·A(τ) uses an expansion of τ·A(τ) in terms of expansion basis functions having respective unknown coefficients defined by a vector β, where Mβ=c, where c comprises a vector representation of said measurements of magnetic field, $B(r_i)$ at sensor positions $r_i$, and where elements M(i,j) of matrix M are defined by a combination of a jth respective basis function and said position $r_i$, wherein M represents the geometry of the head independent of said current distribution.

13. A method as claimed in claim 12 wherein c further comprises a term comprising
representing an irrotational part of said 3D current distribution in combination with a vectorial geometry-conductivity function for said head, H(r,τ) dependent on said geometry-conductivity functions for said regions of said head (w(r,τ)).

14. A method as claimed in claim 1 wherein said modelling comprises modelling the head as three or more regions, an innermost region of the head defining a cerebellum region, the next regions defining, in order, two or more of: a cerebrospinal fluid shell region, a skull bone shell region, and a scalp shell region.

15. Apparatus for processing an EEG and/or MEG signal to generate image data representing a 3D current distribution, J, within the brain, the apparatus comprising:
an input to receive a plurality of captured electric and/or magnetic measurements from the exterior of the head; and
a processor coupled to said input, to an output, to working memory and to program memory storing processor control code, wherein the stored code comprises code to: solve an integral equation for a part of said current distribution to generate said image data representing said 3D current distribution, wherein said integral equation comprises an integral of a first function representing said part of said current distribution and of a second function ($\nabla_\tau v_s(r,\tau)$) representing the geometry and conductivity of the head independent of said current distribution;

wherein said solving comprises:

modelling the head as at least two regions separated by at least one internal boundary, and solving a set of partial differential equations, one for each said internal region, each partial differential equation comprising a geometry-conductivity function ($w(r,\tau)$) representing the geometry and conductivity of the respective region, wherein said solving is subject to a boundary condition that either i) the gradients of the functions across the or each said internal boundary are smooth when conductivity is taken into account, or ii) a normal component of the electric field of said part of said current distribution is continuous across the or each said internal boundary, and wherein said geometry-conductivity function for an outermost said region of said head defines said second function ($\nabla_\tau v_s(r,\tau)$); and output said image data, wherein said image data comprises data representing a part of said 3D current distribution.

16. Apparatus for processing an EEG signal to generate image data representing a 3D current distribution, J, within the brain, the apparatus comprising:

an input to receive a plurality of measurements of electric potential on the scalp (b); and a processor coupled to said input, to an output, to working memory and to program memory storing processor control code, wherein the stored code comprises code to:

use a representation of a part of said current distribution as an expansion having a series of unknown coefficients, $\lambda$, of expansion basis functions, where b is dependent on a product of a matrix E and $\lambda$, and where E represents the geometry and conductivity of the head independent of said current distribution, wherein said geometry includes at least one internal boundary within the head, to solve an equation combining b and E·$\lambda$ to determine an estimate of $\lambda$, wherein $\lambda$ defines said 3D current distribution;

wherein E·$\lambda$ represents $$\int_{\Omega_c} (\nabla^2 \Psi(\tau)) v_s(r,\tau) dV(\tau)$$

where $\psi$ is a scalar value representing J, where $v_s(r,\tau)$ is a function representing the geometry and conductivity of the head independent of said current distribution, $\Omega_c$ denotes the region of the brain over which the current distribution is determined, r lies on the surface of the scalp on which EEG measurements are made, and $\tau$ is a dummy variable; and wherein, in said matrix E, a value of an element of the matrix E is defined by an integral, over a region including said current distribution, of a gradient of a said expansion basis function and a function $w_s(r,\tau)$ representing $v_s(r,\tau)$; where $w_s(r,\tau)$ alternatively represents the geometry and conductivity of the head independent of said current distribution, wherein a function $w(r,\tau)$ is determined for each internal region of the head defined by said at least one internal boundary, wherein $w_s(r,\tau)$ is the outermost said function $w(r,\tau)$, and wherein $w_s(r,\tau)$ is determined subject to the constraint that, when conductivity is taken into account, the gradients of the functions $w(r,\tau)$ on either side of different regions of the head separated by a said internal boundary are smooth across each said internal boundary such that a normal component of electric field is continuous across each said internal boundary; and output image data representing said 3D current distribution determined from said estimate of $\lambda$.

17. Apparatus as claimed in claim 16 wherein said functions $w(r,\tau)$ for each internal region of the head are determined by solving a set of partial differential equations for a set of functions $w_j(r,\tau)$, one for each said region where j labels a region, wherein the partial differential equation for each said region except the innermost comprises Laplace's equation for the respective function $w_j(r,\tau)$, and wherein the partial differential equation for the innermost said region comprises Poisson's equation for the innermost region function $w_{innermost}(r,\tau)$; and wherein said solving is subject to a boundary condition that across each said internal boundary a normal component of electric field is continuous.

18. Apparatus as claimed in claim 16 wherein said equation combining b and E·$\lambda$ is b=E·$\lambda$ and wherein said expansion basis functions comprise radial basis functions.

19. A medical imaging device comprising the apparatus of claim 16 and a display to display said image data representing said 3D current distribution within the brain.

* * * * *